US009371522B2

(12) United States Patent
Camire

(10) Patent No.: US 9,371,522 B2
(45) Date of Patent: Jun. 21, 2016

(54) COMPOSITIONS AND METHODS FOR MODULATING HEMOSTASIS

(71) Applicant: The Children's Hospital of Philadelphia, Philadelphia, PA (US)

(72) Inventor: Rodney M. Camire, Sicklerville, NJ (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 14/348,854

(22) PCT Filed: Oct. 1, 2012

(86) PCT No.: PCT/US2012/058279
§ 371 (c)(1),
(2) Date: Mar. 31, 2014

(87) PCT Pub. No.: WO2013/049804
PCT Pub. Date: Apr. 4, 2013

(65) Prior Publication Data
US 2014/0248259 A1  Sep. 4, 2014

Related U.S. Application Data

(60) Provisional application No. 61/541,412, filed on Sep. 30, 2011.

(51) Int. Cl.
*A61K 38/36* (2006.01)
*C12N 9/64* (2006.01)

(52) U.S. Cl.
CPC .............. *C12N 9/6432* (2013.01); *A61K 38/36* (2013.01); *C12Y 304/21006* (2013.01)

(58) Field of Classification Search
CPC ...................................................... A61K 38/36
See application file for complete search history.

(56) References Cited

U.S. PATENT DOCUMENTS

| | | | |
|---|---|---|---|
| 6,562,598 | B1 | 5/2003 | Himmelspach et al. |
| 6,573,071 | B1 | 6/2003 | Himmelspach et al. |
| 6,905,846 | B2 | 6/2005 | Himmelspach et al. |
| 6,958,322 | B1 | 10/2005 | Himmelspach et al. |
| 7,220,569 | B2 | 5/2007 | Himmelspach et al. |
| 2003/0138914 | A1* | 7/2003 | Himmelspach et al. ..... 435/69.6 |
| 2003/0181381 | A1 | 9/2003 | Himmelspach et al. |
| 2009/0098119 | A1 | 4/2009 | Lu |
| 2009/0175931 | A1 | 7/2009 | Camire |

FOREIGN PATENT DOCUMENTS

| | | |
|---|---|---|
| EP | 1728798 | 12/2006 |
| FR | 2841904 A1 | 1/2004 |
| WO | 98/38317 | 9/1998 |
| WO | 98/38318 | 9/1998 |
| WO | 01/70763 | 9/2001 |
| WO | 2004/005347 | 1/2004 |
| WO | WO 2007/059513 * | 5/2007 ............... C12N 9/64 |
| WO | 2012/117203 A1 | 9/2012 |

OTHER PUBLICATIONS

Al-Tamimi, M., Grigoriadis, G., Tran, H., Paul, E., Servadi, P., Berndt, M., Gardiner, E., Andrews, R. "Coagulation-induced shedding of platelet glycoprotein VI mediated by factor Xa." Blood, Apr. 7, 2011, p. 3912-3920, 117(14).
Toso, R., et al. "Alteration of the factor X zymogen to protease transition provides evidence for allosteric linkage between the S1 and FVa binding sites." Blood (2005) 106(11):Abstract 30.
Genbank Accession No. Q5JVE7, "Coagulation Factor X" (2005).
Genbank Accession No. CAA74031.1, "Chymotrypsin [*Homo sapiens*]", (1997).
Friedrich, R., et al. "Staphylocoagulase is a prototype for the mechanism of cofactor induced zymogen activation." Nature (2003) 425: 535-539.
Holt, K., GenBank Q5JVE7 (2005).
Sun, T., et al. "Vitamin K epoxide reductase significantly improves carboxylation in a cell line overexpressing factor X." Blood (2005) 106(12):3811-3815.
Camire, R., et al. "Enhanced gamma-carboxylation of recombinant factor X using a chimeric construct containing the prothromcin propeptide." Biochemistry (2000) 39(46): 14322-14329.
Camire, R. "Prothrombinase assembly and S1 site occupation restore the catalytic activity of FXa impaired by mutation at the sodium-binding site." Journal of Biological Chemistry (2002) 277(40):37863-37870.
Hedstrom, L., et al. "Hydrophobic interactions control zymogen activation in the trypsin family of serine proteases." Biochemistry (1996) 35(14): 4515-4523.
Toso, R., et al. "Factor VII mutant V154G models a zymogen-like form of factor VIIa." The Biochemical Journal (2003) 369(3):563-571.
Toso, R., et al. "Factor VII variants as tools to study Factor VIIa salt bridge formation." Database Biosis. Biosciences, Information Service, Philadelphia, PA & Blood (2001) 98(11):526a [Abstract].
Toso, R., et al. "Alteration of the factor X zymogen to protease transition provides evidence for allosteric linkage between the S1 and FVa binding sites." Blood (2005) 106(11):13A.
Toso, R., et al. "The conformational switch from the factor X zymogen to protease state mediates exosite expression and prothrombinase assembly." Journal of Biological Chemistry (2008) 283(17):18627-18635.
Wells, J.A., "Additivity of Mutational effects in Proteins" (1990) Biochemistry 29(37):8509-8517.
Guo, H.H., et al., "Protein Tolerance to random Amino Acid Change," PNAS (2004) 101:9205-9210.
Hult, K., "Engineered Enzymes for Improved Organic Synthesis," Curr. Opin. Biotech. (2003) 14:395-400.
Stanberg, L., et al., "Variants of Tissue-type Plasminogen Activator with Substantially Enhanced Response and Selectivity toward Fibrin Co-factors," J. Biol. Chem. (1995) 270(40):23444-23449.
Bianchini, E.P., et al., "Mapping of the Catalytic Groove Preferences of Factor Xa Reveals an Inadequate Selectivity for its Macromolecular Substrates" J. Biol. Chem. (2002) 277(23):20527-20534.

(Continued)

*Primary Examiner* — Amber D Steele
(74) *Attorney, Agent, or Firm* — Robert C. Netter, Jr.; Dann, Dorfman, Herrell & Skillman

(57) ABSTRACT

Factor X/Xa variants and methods of use thereof are disclosed.

41 Claims, 13 Drawing Sheets

(56) References Cited

OTHER PUBLICATIONS

Rudinger, J., "Characteristics of the Amino Acids as Components of a Peptide Hormone Sequence" in Peptide Hormones, J.A. Parsons (ed.), Univ. Park Press, Baltimore, pp. 1-7 (1976).
Sziegoliet, A., GenBank CAA74031.1 (1997).
Rudolph, A.E., et al., "Expression, Purification, and Characterization of Recombinant Human Factor X," Protein Expressions Purif. (1997) 10:373-378.
Ngo, J.T., "Computational Complexity, Protein Structure Prediction, and the Levinthal Paradox" in Peptide Hormones, J.A. Parsons (ed.), Univ. Park Press, Baltimore, pp. 491-495 (1976).
Ivanciu, L., et al. "Correction of the Coagulation Defect in Hemophilia using a Factor Xa Variant with Novel Engineered Protease Function," Nat. Biotechnol. (2011) 29(11):1028-1033.
Bunce, M.W., "Zymogen-like Factor Xa Variants Restore Thrombin Generation and Effectively Bypass the Intrinsic Pathway in Vitro," Blood (2011) 117(1):290-298.

* cited by examiner

```
MetGlyArgProLeu  HisLeuValLeuLeu  SerAlaSerLeuAla  GlyLeuLeuLeuLeu
GlyGluSerLeuPhe  IleArgArgGluGln  AlaAsnAsnIleLeu  AlaArgValArgArg
AlaAsnSerPheLeu  GluGluMetLysLys  GlyHisLeuGluArg  GluCysMetGluGlu
ThrCysSerTyrGlu  GluAlaArgGluVal  PheGluAspSerAsp  LysThrAsnGluPhe
TrpAsnLysTyrLys  AspGlyAspGlnCys  GluThrSerProCys  GlnAsnGlnGlyLys
CysLysAspGlyLeu  GlyGluTyrThrCys  ThrCysLeuGluGly  PheGluGlyLysAsn
CysGluLeuPheThr  ArgLysLeuCysSer  LeuAspAsnGlyAsp  CysAspGlnPheCys
HisGluGluGlnAsn  SerValValCysSer  CysAlaArgGlyTyr  ThrLeuAlaAspAsn
GlyLysAlaCysIle  ProThrGlyProTyr  ProCysGlyLysGln  ThrLeuGluArgArg
LysArgSerValAla  GlnAlaThrSerSer  SerGlyGluAlaPro  AspSerIleThrTrp
LysProTyrAspAla  AlaAspLeuAspPro  ThrGluAsnProPhe  AspLeuLeuAspPhe
AsnGlnThrGlnPro  GluArgGlyAspAsn  AsnLeuThrArg__Ile__  __ValGlyGly__GlnGlu
CysLysAspGlyGlu  CysProTrpGlnAla  LeuLeuIleAsnGlu  GluAsnGluGlyPhe
CysGlyGlyThrIle  LeuSerGluPheTyr  IleLeuThrAlaAla  HisCysLeuTyrGln
AlaLysArgPheLys  ValArgValGlyAsp  ArgAsnThrGluGln  GluGluGlyGlyGlu
AlaValHisGluVal  GluValValIleLys  HisAsnArgPheThr  LysGluThrTyrAsp
PheAspIleAlaVal  LeuArgLeuLysThr  ProIleThrPheArg  MetAsnValAlaPro
AlaCysLeuProGlu  ArgAspTrpAlaGlu  SerThrLeuMetThr  GlnLysThrGlyIle
ValSerGlyPheGly  ArgThrHisGluLys  GlyArgGlnSerThr  ArgLeuLysMetLeu
GluValProTyrVal  AspArgAsnSerCys  LysLeuSerSerSer  PheIleIleThrGln
AsnMetPheCysAla  GlyTyrAspThrLys  GlnGluAspAlaCys  GlnGly__Asp__SerGly
GlyProHisValThr  ArgPheLysAspThr  TyrPheValThrGly  IleValSerTrpGly
GluGlyCysAlaArg  LysGlyLysTyrGly  IleTyrThrLysVal  ThrAlaPheLeuLys
TrpIleAspArgSer  MetLysThrArgGly  LeuProLysAlaLys  SerHisAlaProGlu
ValIleThrSerSer  ProLeuLys
```

Figure 9A

```
AlaAsnSerPheLeu  GluGluMetLysLys  GlyHisLeuGluArg  GluCysMetGluGlu
ThrCysSerTyrGlu  GluAlaArgGluVal  PheGluAspSerAsp  LysThrAsnGluPhe
TrpAsnLysTyrLys  AspGlyAspGlnCys  GluThrSerProCys  GlnAsnGlnGlyLys
CysLysAspGlyLeu  GlyGluTyrThrCys  ThrCysLeuGluGly  PheGluGlyLysAsn
CysGluLeuPheThr  ArgLysLeuCysSer  LeuAspAsnGlyAsp  CysAspGlnPheCys
HisGluGluGlnAsn  SerValValCysSer  CysAlaArgGlyTyr  ThrLeuAlaAspAsn
GlyLysAlaCysIle  ProThrGlyProTyr  ProCysGlyLysGln  ThrLeuGluArg
```
Light chain

```
        SerValAla  GlnAlaThrSerSer  SerGlyGluAlaPro  AspSerIleThrTrp
LysProTyrAspAla  AlaAspLeuAspPro  ThrGluAsnProPhe  AspLeuLeuAspPhe
AsnGlnThrGlnPro  GluArgGlyAspAsn  AsnLeuThrArgIle  ValGlyGlyGlnGlu
CysLysAspGlyGlu  CysProTrpGlnAla  LeuLeuIleAsnGlu  GluAsnGluGlyPhe
CysGlyGlyThrIle  LeuSerGluPheTyr  IleLeuThrAlaAla  HisCysLeuTyrGln
AlaLysArgPheLys  ValArgValGlyAsp  ArgAsnThrGluGln  GluGluGlyGlyGlu
AlaValHisGluVal  GluValValIleLys  HisAsnArgPheThr  LysGluThrTyrAsp
PheAspIleAlaVal  LeuArgLeuLysThr  ProIleThrPheArg  MetAsnValAlaPro
AlaCysLeuProGlu  ArgAspTrpAlaGlu  SerThrLeuMetThr  GlnLysThrGlyIle
ValSerGlyPheGly  ArgThrHisGluLys  GlyArgGlnSerThr  ArgLeuLysMetLeu
GluValProTyrVal  AspArgAsnSerCys  LysLeuSerSerSer  PheIleIleThrGln
AsnMetPheCysAla  GlyTyrAspThrLys  GlnGluAspAlaCys  GlnGlyAspSerGly
GlyProHisValThr  ArgPheLysAspThr  TyrPheValThrGly  IleValSerTrpGly
GluGlyCysAlaArg  LysGlyLysTyrGly  IleTyrThrLysVal  ThrAlaPheLeuLys
TrpIleAspArgSer  MetLysThrArgGly  LeuProLysAlaLys  SerHisAlaProGlu
ValIleThrSerSer  ProLeuLys
```
Heavy chain

Figure 9B

AlaAsnSerPheLeu GluGluMetLysLys GlyHisLeuGluArg GluCysMetGluGlu
ThrCysSerTyrGlu GluAlaArgGluVal PheGluAspSerAsp LysThrAsnGluPhe
TrpAsnLysTyrLys AspGlyAspGlnCys GluThrSerProCys GlnAsnGlnGlyLys
CysLysAspGlyLeu GlyGluTyrThrCys ThrCysLeuGluGly PheGluGlyLysAsn
CysGluLeuPheThr ArgLysLeuCysSer LeuAspAsnGlyAsp CysAspGlnPheCys
HisGluGluGlnAsn SerValValCysSer CysAlaArgGlyTyr ThrLeuAlaAspAsn
GlyLysAlaCysIle ProThrGlyProTyr ProCysGlyLysGln ThrLeuGluArg

Light chain

Ile ValGlyGlyGlnGlu
CysLysAspGlyGlu CysProTrpGlnAla LeuLeuIleAsnGlu GluAsnGluGlyPhe
CysGlyGlyThrIle LeuSerGluPheTyr IleLeuThrAlaAla HisCysLeuTyrGln
AlaLysArgPheLys ValArgValGlyAsp ArgAsnThrGluGln GluGluGlyGlyGlu
AlaValHisGluVal GluValValIleLys HisAsnArgPheThr LysGluThrTyrAsp
PheAspIleAlaVal LeuArgLeuLysThr ProIleThrPheArg MetAsnValAlaPro
AlaCysLeuProGlu ArgAspTrpAlaGlu SerThrLeuMetThr GlnLysThrGlyIle
ValSerGlyPheGly ArgThrHisGluLys GlyArgGlnSerThr ArgLeuLysMetLeu
GluValProTyrVal AspArgAsnSerCys LysLeuSerSerSer PheIleIleThrGln
AsnMetPheCysAla GlyTyrAspThrLys GlnGluAspAlaCys GlnGlyAspSerGly
GlyProHisValThr ArgPheLysAspThr TyrPheValThrGly IleValSerTrpGly
GluGlyCysAlaArg LysGlyLysTyrGly IleTyrThrLysVal ThrAlaPheLeuLys
TrpIleAspArgSer MetLysThrArgGly LeuProLysAlaLys SerHisAlaProGlu
ValIleThrSerSer ProLeuLys

Heavy chain

Figure 9C

```
ATGGGGCGC CCACTGCACC TCGTCCTGCT CAGTGCCTCC CTGGCTGGCC TCCTGCTGCT CGGGGAAAGT
CTGTTCATCC GCAGGGAGCA GGCCAACAAC ATCCTGGCGA GGGTCAGGAG GGCCAATTCC TTTCTTGAAG
AGATGAAGAA AGGACACCTC GAAAGAGAGT GCATGGAAGA GACCTGCTCA TACGAAGAGG CCCGCGAGGT
CTTTGAGGAC AGCGACAAGA CGAATGAATT CTGGAATAAA TACAAAGATG GCGACCAGTG TGAGACCAGT
CCTTGCCAGA ACCAGGGCAA ATGTAAAGAC GGCCTCGGGG AATACACCTG CACCTGTTTA GAAGGATTCG
AAGGCAAAAA CTGTGAATTA TTCACACGGA AGCTCTGCAG CCTGGACAAC GGGGACTGTG ACCAGTTCTG
CCACGAGGAA CAGAACTCTG TGGTGTGCTC CTGCGCCCGC GGGTACACCC TGGCTGACAA CGGCAAGGCC
TGCATTCCCA CAGGGCCCTA CCCCTGTGGG AAACAGACCC TGGAACGCAG GAAGAGGTCA GTGGCCCAGG
CCACCAGCAG CAGCGGGGAG GCCCCTGACA GCATCACATG GAAGCCATAT GATGCAGCCG ACCTGGACCC
CACCGAGAAC CCCTTCGACC TGCTTGACTT CAACCAGACG CAGCCTGAGA GGGGCGACAA CAACCTCACG
CGTATCGTGG GAGGCCAGGA ATGCAAGGAC GGGGAGTGTC CTGGCAGGC CCTGCTCATC AATGAGGAAA
ACGAGGGTTT CTGTGGTGGA ACTATTCTGA GCGAGTTCTA CATCCTAACG GCAGCCCACT GTCTCTACCA
AGCCAAGAGA TTCAAGGTGA GGGTAGGTGA CCGGAACACG GAGCAGGAGG AGGGCGGTGA GGCGGTGCAC
GAGGTGGAGG TGGTCATCAA GCACAACCGG TTCACAAAGG AGACCTATGA CTTCGACATC GCCGTGCTCC
GGCTCAAGAC CCCCATCACC TTCCGCATGA ACGTGGCGCC TGCCTGCCTC CCCGAGCCTG ACTGGGCCGA
GTCCACGCTG ATGACGCAGA AGACGGGGAT TGTGAGCGGC TTCGGGCGCA CCCACGAGAA GGGCCGGCAG
TCCACCAGGC TCAAGATGCT GGAGGTGCCC TACGTGGACC GCAACAGCTG CAAGCTGTCC AGCAGCTTCA
TCATCACCCA GAACATGTTC TGTGCCGGCT ACGACACCAA GCAGGAGGAT GCCTGCCAGG GGGACAGCGG
GGGCCCGCAC GTCACCCGCT TCAAGGACAC CTACTTCGTG ACAGGCATCG TCAGCTGGGG AGAGGGCTGT
GCCCGTAAGG GGAAGTACGG GATCTACACC AAGGTCACCG CCTTCCTCAA GTGGATCGAC AGGTCCATGA
AAACCAGGGG CTTGCCCAAG GCCAAGAGCC ATGCCCCGGA GGTCATAACG TCCTCTCCAT TAAAGTGA
```

Figure 9D

US 9,371,522 B2

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 1

Ile Val Gly Gly
 1

<210> SEQ ID NO 2
<211> LENGTH: 488
<212> TYPE: PRT
<213> ORGANISM: Homo sapiens

<400> SEQUENCE: 2

Met Gly Arg Pro Leu His Leu Val Leu Leu Ser Ala Ser Leu Ala Gly
 1               5                  10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60
```

```
Glu Glu Ala Arg Glu Val Phe Glu Asp Ser Asp Lys Thr Asn Glu Phe
 65                  70                  75                  80

Trp Asn Lys Tyr Lys Asp Gly Asp Gln Cys Glu Thr Ser Pro Cys Gln
                 85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
            115                 120                 125

Cys Ser Leu Asp Asn Gly Asp Cys Asp Gln Phe Cys His Glu Glu Gln
            130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
            195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
            275                 280                 285

Gly Asp Arg Asn Thr Glu Gln Glu Glu Gly Gly Glu Ala Val His Glu
            290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
            355                 360                 365

Glu Lys Gly Arg Gln Ser Thr Arg Leu Lys Met Leu Glu Val Pro Tyr
            370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
            435                 440                 445

Tyr Gly Ile Tyr Thr Lys Val Thr Ala Phe Leu Lys Trp Ile Asp Arg
            450                 455                 460

Ser Met Lys Thr Arg Gly Leu Pro Lys Ala Lys Ser His Ala Pro Glu
465                 470                 475                 480

Val Ile Thr Ser Ser Pro Leu Lys
```

<210> SEQ ID NO 3
<211> LENGTH: 139
<212> TYPE: PRT
<213> ORGANISM: Homo sapiens

<400> SEQUENCE: 3

```
Ala Asn Ser Phe Leu Glu Glu Met Lys Lys Gly His Leu Glu Arg Glu
  1               5                  10                  15

Cys Met Glu Glu Thr Cys Ser Tyr Glu Glu Ala Arg Glu Val Phe Glu
             20                  25                  30

Asp Ser Asp Lys Thr Asn Glu Phe Trp Asn Lys Tyr Lys Asp Gly Asp
         35                  40                  45

Gln Cys Glu Thr Ser Pro Cys Gln Asn Gln Gly Lys Cys Lys Asp Gly
     50                  55                  60

Leu Gly Glu Tyr Thr Cys Thr Cys Leu Glu Gly Phe Glu Gly Lys Asn
 65                  70                  75                  80

Cys Glu Leu Phe Thr Arg Lys Leu Cys Ser Leu Asp Asn Gly Asp Cys
                 85                  90                  95

Asp Gln Phe Cys His Glu Glu Asn Ser Val Val Cys Ser Cys Ala
                100                 105                 110

Arg Gly Tyr Thr Leu Ala Asp Asn Gly Lys Ala Cys Ile Pro Thr Gly
            115                 120                 125

Pro Tyr Pro Cys Gly Lys Gln Thr Leu Glu Arg
        130                 135
```

<210> SEQ ID NO 4
<211> LENGTH: 306
<212> TYPE: PRT
<213> ORGANISM: Homo sapiens

<400> SEQUENCE: 4

```
Ser Val Ala Gln Ala Thr Ser Ser Ser Gly Glu Ala Pro Asp Ser Ile
  1               5                  10                  15

Thr Trp Lys Pro Tyr Asp Ala Ala Asp Leu Asp Pro Thr Glu Asn Pro
             20                  25                  30

Phe Asp Leu Leu Asp Phe Asn Gln Thr Gln Pro Glu Arg Gly Asp Asn
         35                  40                  45

Asn Leu Thr Arg Ile Val Gly Gly Gln Glu Cys Lys Asp Gly Glu Cys
     50                  55                  60

Pro Trp Gln Ala Leu Leu Ile Asn Glu Glu Asn Glu Gly Phe Cys Gly
 65                  70                  75                  80

Gly Thr Ile Leu Ser Glu Phe Tyr Ile Leu Thr Ala Ala His Cys Leu
                 85                  90                  95

Tyr Gln Ala Lys Arg Phe Lys Val Arg Val Gly Asp Arg Asn Thr Glu
                100                 105                 110

Gln Glu Glu Gly Gly Glu Ala Val His Glu Val Glu Val Val Ile Lys
            115                 120                 125

His Asn Arg Phe Thr Lys Glu Thr Tyr Asp Phe Asp Ile Ala Val Leu
        130                 135                 140

Arg Leu Lys Thr Pro Ile Thr Phe Arg Met Asn Val Ala Pro Ala Cys
145                 150                 155                 160

Leu Pro Glu Arg Asp Trp Ala Glu Ser Thr Leu Met Thr Gln Lys Thr
                165                 170                 175

Gly Ile Val Ser Gly Phe Gly Arg Thr His Glu Lys Gly Arg Gln Ser
```

```
            180                 185                 190
Thr Arg Leu Lys Met Leu Glu Val Pro Tyr Val Asp Arg Asn Ser Cys
            195                 200                 205

Lys Leu Ser Ser Ser Phe Ile Ile Thr Gln Asn Met Phe Cys Ala Gly
            210                 215                 220

Tyr Asp Thr Lys Gln Glu Asp Ala Cys Gln Gly Asp Ser Gly Gly Pro
225                 230                 235                 240

His Val Thr Arg Phe Lys Asp Thr Tyr Phe Val Thr Gly Ile Val Ser
            245                 250                 255

Trp Gly Glu Gly Cys Ala Arg Lys Gly Lys Tyr Gly Ile Tyr Thr Lys
            260                 265                 270

Val Thr Ala Phe Leu Lys Trp Ile Asp Arg Ser Met Lys Thr Arg Gly
            275                 280                 285

Leu Pro Lys Ala Lys Ser His Ala Pro Glu Val Ile Thr Ser Ser Pro
            290                 295                 300

Leu Lys
305

<210> SEQ ID NO 5
<211> LENGTH: 254
<212> TYPE: PRT
<213> ORGANISM: Homo sapiens

<400> SEQUENCE: 5

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
            35                  40                  45

Arg Phe Lys Val Arg Val Gly Asp Arg Asn Thr Glu Gln Glu Glu Gly
        50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
            115                 120                 125

Gly Phe Gly Arg Thr His Glu Lys Gly Arg Gln Ser Thr Arg Leu Lys
130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
            195                 200                 205

Cys Ala Arg Lys Gly Lys Tyr Gly Ile Tyr Thr Lys Val Thr Ala Phe
        210                 215                 220

Leu Lys Trp Ile Asp Arg Ser Met Lys Thr Arg Gly Leu Pro Lys Ala
225                 230                 235                 240
```

Lys Ser His Ala Pro Glu Val Ile Thr Ser Ser Pro Leu Lys
         245                 250

<210> SEQ ID NO 6
<211> LENGTH: 1467
<212> TYPE: DNA
<213> ORGANISM: Homo sapiens

<400> SEQUENCE: 6

| | | | | | |
|---|---|---|---|---|---|
| atggggcgcc | cactgcacct | cgtcctgctc | agtgcctccc | tggctggcct | cctgctgctc       60 |
| ggggaaagtc | tgttcatccg | cagggagcag | gccaacaaca | tcctggcgag | ggtcaggagg      120 |
| gccaattcct | ttcttgaaga | gatgaagaaa | ggacacctcg | aaagagagtg | catggaagag      180 |
| acctgctcat | acgaagaggc | ccgcgaggtc | tttgaggaca | cgacaagac  | gaatgaattc      240 |
| tggaataaat | acaagatgg  | cgaccagtgt | gagaccagtc | cttgccagaa | ccagggcaaa      300 |
| tgtaaagacg | gcctcgggga | atacacctgc | acctgtttag | aaggattcga | aggcaaaaac      360 |
| tgtgaattat | tcacacggaa | gctctgcagc | ctggacaacg | gggactgtga | ccagttctgc      420 |
| cacgaggaac | agaactctgt | ggtgtgctcc | tgcgcccgcg | ggtacaccct | ggctgacaac      480 |
| ggcaaggcct | gcattcccac | agggccctac | ccctgtggga | aacagaccct | ggaacgcagg      540 |
| aagaggtcag | tgcccaggc  | caccagcagc | agcggggagg | ccctgacag  | catcacatgg      600 |
| aagccatatg | atgcagccga | cctggacccc | accgagaacc | ccttcgacct | gcttgacttc      660 |
| aaccagacgc | agcctgagag | gggcgacaac | aacctcacgc | gtatcgtggg | aggccaggaa      720 |
| tgcaaggacg | gggagtgtcc | ctggcaggcc | ctgctcatca | tgaggaaaa  | cgagggtttc      780 |
| tgtggtggaa | ctattctgag | cgagttctac | atcctaacgg | cagcccactg | tctctaccaa      840 |
| gccaagagat | tcaaggtgag | ggtaggtgac | cggaacacgg | agcaggagga | gggcggtgag      900 |
| gcggtgcacg | aggtggaggt | ggtcatcaag | cacaaccggt | tcacaaagga | gacctatgac      960 |
| ttcgacatcg | ccgtgctccg | gctcaagacc | cccatcacct | tccgcatgaa | cgtggcgcct     1020 |
| gcctgcctcc | ccgagcgtga | ctgggccgag | tccacgctga | tgacgcagaa | gacggggatt     1080 |
| gtgagcggct | tcgggcgcac | ccacgagaag | ggccggcagt | ccaccaggct | caagatgctg     1140 |
| gaggtgccct | acgtggaccg | caacagctgc | aagctgtcca | gcagcttcat | catcacccag     1200 |
| aacatgttct | gtgccggcta | cgacaccaag | caggaggatg | cctgccaggg | ggacagcggg     1260 |
| ggcccgcacg | tcacccgctt | caaggacacc | tacttcgtga | caggcatcgt | cagctgggga     1320 |
| gagggctgtg | cccgtaaggg | gaagtacggg | atctacacca | aggtcaccgc | cttcctcaag     1380 |
| tggatcgaca | ggtccatgaa | aaccaggggc | ttgcccaagg | ccaagagcca | tgccccggag     1440 |
| gtcataacgt | cctctccatt | aaagtga    |            |            |           1467 |

<210> SEQ ID NO 7
<211> LENGTH: 6
<212> TYPE: PRT
<213> ORGANISM: Artificial Sequence
<220> FEATURE:
<223> OTHER INFORMATION: proteolytic cleavage site

<400> SEQUENCE: 7

Arg Lys Arg Arg Lys Arg
 1               5

COMPOSITIONS AND METHODS FOR MODULATING HEMOSTASIS

This application is a §371 application of PCT/US2012/058279, filed Oct. 1, 2012, which claims priority under 35 U.S.C. §119(e) to U.S. Provisional Patent Application No. 61/541,412, filed Sep. 30, 2011. The foregoing applications are incorporated by reference herein.

This invention was made with government support under Grant Numbers P01 HL-74124 awarded by the National Institutes of Health. The government has certain rights in the invention.

FIELD OF THE INVENTION

The present invention relates to the fields of medicine and hematology. More specifically, the invention provides novel coagulation Factor X/Xa variants and methods of using the same to modulate the coagulation cascade in patients in need thereof.

BACKGROUND OF THE INVENTION

Several publications and patent documents are cited throughout the specification in order to describe the state of the art to which this invention pertains. Each of these citations is incorporated herein by reference as though set forth in full.

In vertebrates with a closed circulatory system, an elaborate mechanism involving cellular components as well as circulating plasma proteins has evolved to prevent significant blood loss following injury. The response to damage needs to be focused and commensurate with the extent of injury. In these schemes, coagulation proceeds through a series of proteolytic reactions involving enzymes that become activated, culminating in the generation of the final enzyme thrombin which activates platelets and cleaves a structural protein (fibrinogen) to generate a fibrin, providing a meshwork which physically prevents blood from leaving the vessel. Fibrin formation and platelet activation represent a major defense and repair mechanism, which ensures the integrity of vascular system. Deficiency of proteins that lead to the formation of thrombin can cause bleeding complications. One of the most common types of bleeding disorders is hemophilia A and B. Hemophilia A is characterized by a deficiency in coagulation factor VIII and hemophilia B is characterized by factor IX deficiency. Current therapy for hemophilia is carried out by replacement of the defective or missing coagulation factors. Unfortunately, some patients (~3-20%) develop high-titer, inhibitory antibodies to the infused factor VIII or factor IX. Development of inhibitors against the administrated proteins represents a severe problem in the management of hemophilia. In these so-called inhibitor patients alternative strategies have been developed which bypass the intrinsic pathway such as activated prothrombin complex concentrates (aPCCs) and recombinant FVIIa (NovoSeven®). These products work by accelerating FXa formation and ultimately thrombin generation thereby providing adequate hemostasis. Because of a whole host of issues including short half-life, effective dose range, cost and potential for thrombotic complications other approaches should be explored. An alternative approach could be to infuse FXa directly; however it has a very short half-life in plasma and has the potential to activate multiple upstream pathways leading to a disseminated hemostatic response.

SUMMARY OF THE INVENTION

In accordance with the present invention, compositions and methods are provided for influencing regulatory sites in the FX zymogen to protease transition pathway thereby driving production of a more "zymogen-like" FXa species. The compositions and methods of the invention are effective to modulate hemostasis in patients in need thereof.

In one embodiment, variant Factor X/Factor Xa zymogens/proteases which modulate hemostasis are provided. In a particular embodiment, the variant comprises at least one modification selected from the group consisting of a) the Ile at position 16 is Thr or Met; and b) the Val at position 17 is Thr or Ser. Nucleic acids encoding the variants of the invention are also disclosed as are methods of use thereof. Such nucleic acid molecules may optionally encode an intracellular PACE/furin cleavage site. Another aspect of the invention includes host cells expressing the variant of the invention. Methods for isolating and purifying the variants are also disclosed.

Pharmaceutical compositions comprising the variants of the invention in a carrier are also provided. The invention also includes methods for the treatment of a hemostasis related disorder in a patient in need thereof comprising administration of a therapeutically effective amount of the variant containing pharmaceutical compositions described herein. Such methods have efficacy in the treatment of disorders where a pro-coagulant is needed and include, without limitation, hemophilia A and B.

BRIEF DESCRIPTION OF THE DRAWINGS

FIG. 4 provides graphs demonstrating that FXa variants restore thrombin generation in hemophilia B plasma.

FIG. 9A provides an amino acid sequence of human Pre-Pro-Factor X (SEQ ID NO: 2). The underlined and bolded residues are positions 16, 17, 18, 19, and 194 in chymotrypsin numbering. FIG. 9B provides an amino acid sequence of the light chain (SEQ ID NO: 3) and heavy chain (SEQ ID NO: 4)

of Factor X. FIG. 9C provides an amino acid sequence of the light chain (SEQ ID NO: 3) and heavy chain (SEQ ID NO: 5) of activated Factor X (FXa). FIG. 9D provides a nucleic acid sequence (SEQ ID NO: 6) which encodes human FX preproprotein.

DETAILED DESCRIPTION OF THE INVENTION

Figure 1:
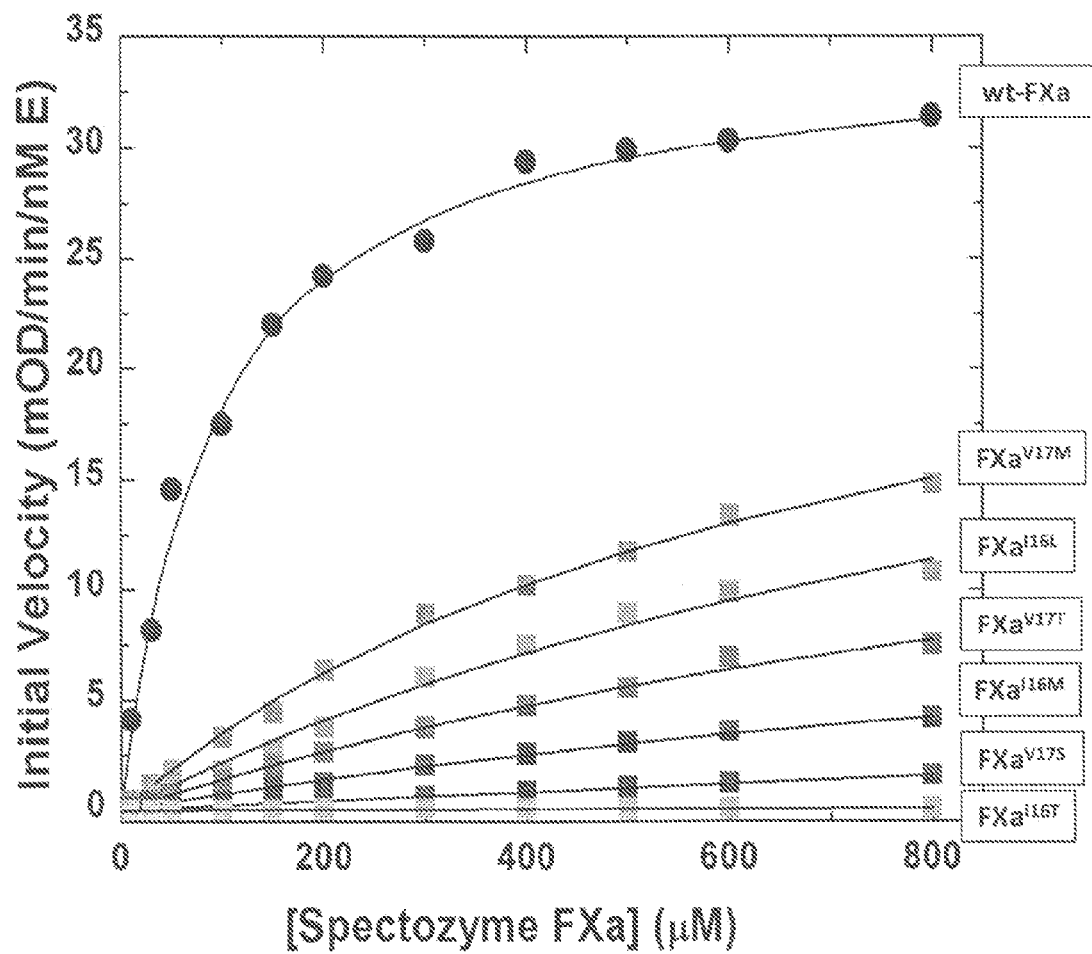
FIG. 1 provides a graph of the initial velocity of wild-type FXa and various FXa variants at different concentrations of substrate Spectrozyme® FXa.

Factor X (FX) is a serine protease zymogen and is a substrate for both the extrinsic (tissue factor/FVIIa) and intrinsic (FVIIIa/FIXa) tenase enzyme complexes which cleave the $Arg^{15}$-$Ile^{16}$ scissile bond in FX releasing a 52-amino acid activation peptide generating FXa. Factor Xa is the protease responsible for the conversion of prothrombin to thrombin. All serine protease zymogens are inactive because a portion of their structure (i.e. activation domain), including part of the substrate binding site, is disordered and is not readily available for ligand binding. Activation of these zymogens by limited proteolysis at a very specific site (position 16, using the chymotrypsin numbering system) results in a major conformational change, ordering this "activation domain" and allowing for strong ligand binding at this region (see, e.g., Furie et al. (1976) J. Biol. Chem., 251:6807-6814; Robison et al. (1980) J. Biol. Chem., 255:2014-2021; Keyt et al. (1982) J. Biol. Chem., 257:8687-8695; Persson et al. (1991) J. Biol. Chem., 266:2458; Persson et al. (1993) J. Biol. Chem., 268:22531-22539; Dahlback et al. (1978) Biochem., 17:4938-4945). This zymogen to protease transition is generally the same for all serine proteases, following a mechanism by which cleavage at position 16 liberates a new N-terminus (e.g., the sequence IVGG (SEQ ID NO: 1) for wild-type Factor X) which then intramolecularly binds to a specific site within the activation domain (Asp194). It has been shown that strong ligands which bind to the activation domain of the zymogen, stabilize this region and at least partially mimic the changes seen in the zymogen to protease transition. Additionally, it has been shown that IVGG (SEQ ID NO: 1) peptides can at least partially activate trypsinogen (zymogen) in the absence of cleavage at position 16.

Recently, FXa variants have been generated that alter this zymogen to protease transition, yet efficiently restore thrombin generation in hemophilia. These derivatives have mutations at the beginning of the heavy chain at positions 16 or 17 (chymotrypsin numbering system) (PCT/US2006/060927). Biochemical characterization shows that the variants FXaI16L and FXaV17A are "zymogen-like" and have poor active site function and low reactivity towards the physiological inhibitors antithrombin III (ATIII) and tissue factor pathway inhibitor (TFPI). Surprisingly, however, the biological activity of the variants can be fully rescued when associated with the cofactor FVa to form prothrombinase. The data show that FXaI16L can restore thrombin generation in hemophilic plasma and has a prolonged half-life (~120 min vs. 1 min for wt-FXa; Toso, et al. (2008) JBC 283:18627-35; Bunce et al. (2011) Blood, 117:290-298). Furthermore, in vivo experiments with hemophilia B (HB) mice show that zymogen-like FXaI16L appears safe and provides adequate hemostasis in multiple injury models (L. Ivanciu and R. Camire, ASH Abstract, 2008; ISTH Abstract, 2009).

However, based upon the nature of the modification and the molecular transition being disrupted, it was determined herein that depending on the amino acid at position 16 or 17, it is possible to generate a series of FXa variants that have more or less 'zymogen-like' character. The potential advantage of a variant being more zymogen-like (relative to FXaI16L) would be an extension of its half-life, safety profile as the variant, in the absence of FVa, would be less active and have a more disordered active site. However, once FVa becomes available following the initiation of coagulation, the cofactor would bind the variant and stabilized the variants and hence rescue its activity.

Herein, a new series of zymogen-like FX variants are provided with desirable properties (e.g., longer half-life in vivo, high efficacy in injury models). The FXa variants may comprise at least one change/substitution at positions 16, 17, 18, 19 and/or 194 (based on chymotrypsin numbering). Specifically, FXa variants with amino acid substitutions at position 16 and/or 17 are provided that advantageous properties relative to FXa-I16L. These properties may impact pharmacokinetics/pharmacodynamics (PK/PD) in vivo procoagulant activity and/or safety profile, providing a different therapeutic range.

The instant invention encompasses variant FX molecules including FXa variants, FX variants, FX prepropeptide variants, and FX propeptide variants. For simplicity, the variants are generally described throughout the application in the context of FXa. However, the invention contemplates and encompasses FX, FX prepropeptide, and FX propeptide molecules having the same amino acid substitutions.

The FXa variants of the instant invention can be from any mammalian species. In a particular embodiment, the FXa variant is human. GenBank Accession No. NP_000495 provides an example of the wild-type human FX preproprotein. FIG. 9A provides SEQ ID NO: 2, which is an example of the amino acid sequence of the human FX preproprotein. The FX prepropetide comprises a signal peptide from amino acids 1-23 and a propeptide sequence from amino acids 24-40. The cleavage of the propeptide yields a protein with a new terminus sequence of Ala-Asn-Ser. The FX prepropeptide is also cleaved into a mature two-chain form (light and heavy) by the excision at the tripeptide RKR to generate the Factor X zymogen. The two chains are linked via a disulfide bond. FIG. 9B provides SEQ ID NOs: 3 and 4, which are examples of the amino acid sequence of the human FX light and heavy chains, respectively. Factor X is activated by the cleavage of the 52 amino acid activation peptide to yield a new amino-terminal sequence of IVGG (SEQ ID NO: 1) for wild-type FXa heavy chain. FIG. 9C provides SEQ ID NOs: 3 and 5, which are examples of the amino acid sequence of the human FXa light and heavy chains. Notably, the above proteolytic cleavage events may be imprecise, thereby leading to addition or loss of amino acids at the cleavage sites. FIG. 9D provides a nucleic acid sequence (SEQ ID NO: 6) which encodes human FX preproprotein. Nucleic acid molecules which encode FX and FXa can be readily determined from the provided amino acid and nucleotide sequences.

In a particular embodiment, the variant of the instant invention has at least 75%, 80%, 85%, 90%, 95%, 97%, 99%, or 100% homology (identity) with SEQ ID NO: 2, particularly at least 90%, 95%, 97%, or 99% homology. In a particular embodiment, the variant of the instant invention has at least 75%, 80%, 85%, 90%, 95%, 97%, 99%, or 100% homology with amino acids 24-488 of SEQ ID NO: 2, particularly at least 90%, 95%, 97%, or 99% homology. In a particular embodiment, the variant of the instant invention has at least 75%, 80%, 85%, 90%, 95%, 97%, 99%, or 100% homology with amino acids 41-488 of SEQ ID NO: 2, particularly at least 90%, 95%, 97%, or 99% homology. In a particular embodiment, the variant comprises a light and heavy chain, wherein the light chain has at least 75%, 80%, 85%, 90%, 95%, 97%, 99%, or 100% homology with SEQ ID NO: 3, particularly at least 90%, 95%, 97%, or 99% homology, and wherein the heavy chain has at least 75%, 80%, 85%, 90%, 95%, 97%, 99%, or 100% homology with SEQ ID NO: 4, particularly at least 90%, 95%, 97%, or 99% homology. In a particular embodiment, the variant comprises a light and heavy chain, wherein the light chain has at least 75%, 80%, 85%, 90%, 95%, 97%, 99%, or 100% homology with SEQ ID NO: 3, particularly at least 90%, 95%, 97%, or 99% homology, and wherein the heavy chain has at least 75%, 80%, 85%, 90%, 95%, 97%, 99%, or 100% homology with SEQ ID NO: 5, particularly at least 90%, 95%, 97%, or 99% homology. The homology percentages above exclude the substitutions inserted at positions 16 and/or 17.

The variants of the instant invention may also be posttranslationally modified (γ-carboxylation). The variants may be posttranslationally modified in a cell or in vitro.

In a particular embodiment, the variants of the instant invention have an increased half-life in plasma (e.g., hemophilia plasma). In a particular embodiment, the variants of the invention in the absence of FVa are refractory to all active site function and are poor activators. The variants exhibit activity in the presence of FVa.

The FXa variants of the instant invention may comprise at least one substitution at position 16, 17, 18, 19, and/or 194 (by chymotrypsin numbering; positions 235-239 and 418 in FIG. 9A (SEQ ID NO: 2)). In a particular embodiment, the isoleucine at position 16 is substituted with methionine, threonine, or serine. In a particular embodiment, the isoleucine at position 16 is substituted with the threonine or methionine. In a particular embodiment, the isoleucine at position 16 is substituted with threonine. In a particular embodiment, the valine at position 17 is substituted with methionine, threonine, or serine. In a particular embodiment, the valine at position 17 is substituted with the hydroxyl amino acid threonine or serine. In a particular embodiment, the valine at position 17 is substituted with threonine. The variants of the instant invention may comprise at least one of the above substitutions at position 16 and/or 17. The variants of the instant invention may further comprise at least one other substitution (e.g., at position 18, 19, and/or 194). For example, the Asp at position 194 may be replaced with an Asn or Glu.

Nucleic acid molecules encoding the above variants are also encompassed by the instant invention. Nucleic acid molecules encoding the variants may be prepared by any method known in the art. The nucleic acid molecules may be maintained in any convenient vector, particularly an expression vector.

Compositions comprising at least one variant polypeptide and at least one carrier are also encompassed by the instant invention. Compositions comprising at least one variant nucleic acid molecule and at least one carrier are also encompassed by the instant invention. Except insofar as any conventional carrier is incompatible with the variant to be administered, its use in the pharmaceutical composition is contemplated. In a particular embodiment, the carrier is a pharmaceutically acceptable carrier for intravenous administration.

DEFINITIONS

Various terms relating to the biological molecules of the present invention are used hereinabove and also throughout the specification and claims.

The phrase "variant zymogen/protease" refers to a modified FX zymogen or FXa protease which has been genetically altered such that its protease activity when converted to FXa is reduced or "zymogen-like" in the absence of specific cofactors.

The phrase "hemostasis related disorder" refers to bleeding disorders such as, without limitation, hemophilia A, hemophilia B, hemophilia A and B patients with inhibitory antibodies, deficiencies in at least one coagulation factor (e.g., Factors VII, IX, X, XI, V, XII, II, and/or von Willebrand factor), combined FV/FVIII deficiency, vitamin K epoxide reductase C1 deficiency, gamma-carboxylase deficiency; bleeding associated with trauma, injury, thrombosis, thrombocytopenia, stroke, coagulopathy (hypocoagulability), disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzman thromblastemia, and storage pool deficiency.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

With respect to protein, the term "isolated protein" is sometimes used herein. This term may refer to a protein produced by expression of an isolated nucleic acid molecule of the invention. Alternatively, this term may refer to a protein which has been sufficiently separated from other proteins with which it would naturally be associated (e.g., so as to exist in "substantially pure" form).

The term "vector" refers to a carrier nucleic acid molecule (e.g., DNA) into which a nucleic acid sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.), particularly at least 75% by weight, or at least 90-99% or more by weight of the compound of interest. Purity may be measured by methods appropriate for the compound of interest (e.g. chromatographic methods, agarose or polyacrylamide gel electrophoresis, HPLC analysis, and the like).

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

Preparation of Variant Encoding Nucleic Acid Molecules and Polypeptides

A. Nucleic Acid Molecules

Nucleic acid molecules encoding the variants of the invention may be prepared by using recombinant DNA technology methods. The availability of nucleotide sequence information enables preparation of isolated nucleic acid molecules of the invention by a variety of means. For example, nucleic acid sequences encoding a variant may be isolated from appropriate biological sources using standard protocols well known in the art.

Nucleic acids of the present invention may be maintained as DNA in any convenient cloning vector. In a preferred embodiment, clones are maintained in a plasmid cloning/expression vector (e.g., pBluescript (Stratagene, La Jolla, Calif.)), which is propagated in a suitable E. coli host cell. Alternatively, the nucleic acids may be maintained in a vector suitable for expression in mammalian cells. In cases where post-translational modification affects variant function, it is preferable to express the molecule in mammalian cells.

In one embodiment, the nucleic acids encoding the variants of the instant invention may be further modified via insertion of an intracellular proteolytic cleavage site (the instant invention also encompasses the resultant polypeptide both before and after cleavage). In order to express FXa variants in mammalian cells, an intracellular proteolytic cleavage site can be inserted between positions Arg15 and Ile16 in the variant FX. Such cleavage sites include, without limitation: Arg-Lys-Arg or Arg-Lys-Arg-Arg-Lys-Arg. These cleavage sites are efficiently recognized by proteases (PACE/furin-like enzymes) within the cell and are removed. This results in a processed variant FXa in which the heavy chain on the molecule begins at position 16. Introduction of this cleavage site at this position will allow for the intracellular conversion of FX to FXa. In another embodiment, the entire 52 amino acid activation peptide can be removed and the intracellular protease cleavage site can be introduced in its place which will result in variant FXa.

Ultimately these types of modifications allow for secretion of the "active" processed form of variant FX from a cell that expresses the modified variant FX. Secretion of the cleaved factor obviates a need for proteolytic cleavage during blood clotting or following the isolation of the protein.

Variant encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting variant expression.

B. Proteins

The variants of the present invention may be prepared in a variety of ways, according to known methods. The protein may be purified from appropriate sources (e.g., transformed bacterial or animal cultured cells or tissues which express variants), for example, by immunoaffinity purification. However, this is not a preferred method due to the low amount of protein likely to be present in a given cell type at any time.

The availability of nucleic acid molecules encoding the variants enables production of the variants using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, larger quantities of variant may be produced by expression in a suitable prokaryotic or eukaryotic expression system. For example, part or all of a DNA molecule encoding the variant may be inserted into a plasmid vector adapted for expression in a bacterial cell, such as E. coli or a mammalian cell such as CHO or Hela cells. Alternatively, tagged fusion proteins comprising the variant can be generated. Such variant-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as E. coli or a eukaryotic cell, such as, but not limited to, yeast and mammalian cells. Vectors such as those described above comprise the regulatory elements necessary for expression of the DNA in the host cell positioned in such a manner as to permit expression of the DNA in the host cell. Such regulatory elements required for expression include, but are not limited to, promoter sequences, transcription initiation sequences, and enhancer sequences.

Variant proteins, produced by gene expression in a recombinant prokaryotic or eukaryotic system may be purified according to methods known in the art. In a particular embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus Alternative tags may comprise the FLAG epitope, GST or the hemagglutinin epitope. Such methods are commonly used by skilled practitioners.

Variant proteins, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. A variety of expression systems of utility for the methods of the present invention are well known to those of skill in the art.

Accordingly, the present invention also encompasses a method of making a polypeptide (as disclosed), the method including expression from nucleic acid encoding the polypeptide (generally nucleic acid). This may conveniently be achieved by culturing a host cell, containing such a vector, under appropriate conditions which cause or allow production of the polypeptide. Polypeptides may also be produced in in vitro systems, such as in reticulocyte lysates.

Uses of Variant Proteins and Variant-Encoding Nucleic Acids

Variant nucleic acids encoding polypeptides having altered protease activities may be used according to this invention, for example, as therapeutic and/or prophylactic agents (protein or nucleic acid) which modulate the blood coagulation cascade. It is demonstrated herein that the variant molecules can increase coagulation and provide effective hemostasis.

A. Variant Polypeptides

In a particular embodiment of the present invention, variant polypeptides may be administered to a patient via infusion in a biologically compatible carrier, preferably via intravenous injection. The variants of the invention may optionally be encapsulated into liposomes or mixed with other phospholipids or micelles to increase stability of the molecule. Variants may be administered alone or in combination with other agents known to modulate hemostasis (e.g., Factor V, Factor Va or derivatives thereof). An appropriate composition in which to deliver variant polypeptides may be determined by a medical practitioner upon consideration of a variety of physiological variables, including, but not limited to, the patient's condition and hemodynamic state. A variety of compositions well suited for different applications and routes of administration are well known in the art and are described hereinbelow.

The preparation containing the purified variants contains a physiologically acceptable matrix and is preferably formulated as a pharmaceutical preparation. The preparation can be formulated using substantially known prior art methods, it can be mixed with a buffer containing salts, such as NaCl, $CaCl_2$, and amino acids, such as glycine and/or lysine, and in a pH range from 6 to 8. Until needed, the purified preparation containing the variant can be stored in the form of a finished solution or in lyophilized or deep-frozen form. In a particular embodiment, the preparation is stored in lyophilized form and is dissolved into a visually clear solution using an appropriate reconstitution solution. Alternatively, the preparation according to the present invention can also be made available as a liquid preparation or as a liquid that is deep-frozen. The preparation according to the present invention is especially stable, i.e., it can be allowed to stand in dissolved form for a prolonged time prior to application.

The preparation according to the present invention which contains a FX variant in combination with factor XIa or a derivative thereof which is able to activate the FX variant into FXa or the FXa variant can be made available in the form of a combination preparation comprising a container that holds factor XIa which is immobilized on a matrix, potentially in the form of a miniature column or a syringe complemented with a protease, and a container containing the pharmaceutical preparation with the factor X variant. To activate the factor X variant, the factor X variant-containing solution, for example, can be pressed over the immobilized protease. During storage of the preparation, the factor X variant-containing solution is preferably spatially separated from the protease. The preparation according to the present invention can be stored in the same container as the protease, but the components are spatially separated by an impermeable partition which can be easily removed before administration of the preparation. The solutions can also be stored in separate containers and be brought into contact with each other only shortly prior to administration.

The factor X variant can be activated into factor Xa shortly before immediate use, i.e., prior to the administration to the patient. The activation can be carried out by bringing a factor X variant into contact with an immobilized protease or by mixing solutions containing a protease, on the one hand, and the factor X variant, on the other hand. Thus, it is possible to separately maintain the two components in solution and to mix them by means of a suitable infusion device in which the components come into contact with each other as they pass through the device and thereby to cause an activation into factor Xa or into the factor Xa variant. The patient thus receives a mixture of factor Xa and, in addition, a serine protease which is responsible for the activation. In this context, it is especially important to pay close attention to the dosage since the additional administration of a serine protease also activates endogenous factor X, which may shorten the coagulation time.

The preparation according to the present invention can be made available as a pharmaceutical preparation with factor Xa activity in the form of a one-component preparation or in combination with other factors in the form of a multi-component preparation.

Prior to processing the purified protein into a pharmaceutical preparation, the purified protein may be subjected to the conventional quality controls and fashioned into a therapeutic form of presentation. In particular, during the recombinant manufacture, the purified preparation may be tested for the absence of cellular nucleic acids as well as nucleic acids that are derived from the expression vector, particularly using a method, such as is described in EP 0 714 987.

Another feature of this invention relates to making available a preparation which contains a factor Xa variant with a high stability and structural integrity and which, in particular, is free from inactive factor X/Xa intermediates and autoproteolytic degradation products and which can be produced by activating a factor X variant of the type described above and by formulating it into an appropriate preparation.

The pharmaceutical preparation may contain dosages of between about 10-1000 µg/kg, about 10-500 µg/kg, particularly between about 10-250 µg/kg, between 10 and 75 µg/kg, or about 40 µg/kg of the variant polypeptide. The amounts may be administered intravenously at least one a day. Patients may be treated immediately upon presentation at the clinic with a bleed or prior to the delivery of cut/wound causing a bleed. Alternatively, patients may receive a bolus infusion every one to three hours, or if sufficient improvement is observed, a once daily infusion of the variant described herein.

B. Variant-Encoding Nucleic Acids

Variant-encoding nucleic acids may be used for a variety of purposes in accordance with the present invention. In a particular embodiment of the invention, a nucleic acid delivery vehicle (i.e., an expression vector) for modulating blood coagulation is provided wherein the expression vector comprises a nucleic acid sequence coding for a variant polypeptide, or a functional fragment thereof as described herein. Administration of variant-encoding expression vectors to a patient results in the expression of variant polypeptide which serves to alter the coagulation cascade. In accordance with the present invention, a variant encoding nucleic acid sequence may encode a variant polypeptide as described herein whose expression increases hemostasis. In a particular embodiment, the nucleic acid sequence encodes a human Factor Xa polypeptide variant.

Expression vectors comprising variant nucleic acid sequences may be administered alone, or in combination with other molecules useful for modulating hemostasis. According to the present invention, the expression vectors or combination of therapeutic agents may be administered to the patient alone or in a pharmaceutically acceptable or biologically compatible composition.

In a particular embodiment of the invention, the expression vector comprising nucleic acid sequences encoding the variant is a viral vector. Viral vectors which may be used in the present invention include, but are not limited to, adenoviral vectors (with or without tissue specific promoters/enhancers), adeno-associated virus (AAV) vectors of multiple serotypes (e.g., AAV-2, AAV-5, AAV-7, and AAV-8) and hybrid AAV vectors, lentivirus vectors and pseudo-typed lentivirus vectors [e.g., Ebola virus, vesicular stomatitis virus (VSV), and feline immunodeficiency virus (FIV)], herpes simplex virus vectors, vaccinia virus vectors, and retroviral vectors.

In a particular embodiment of the present invention, methods are provided for the administration of a viral vector comprising nucleic acid sequences encoding a variant or a functional fragment thereof. Adenoviral vectors of utility in the methods of the present invention preferably include at least the essential parts of adenoviral vector DNA. As described herein, expression of a variant polypeptide following administration of such an adenoviral vector serves to modulate hemostasis, particularly to enhance the procoagulation activity of the protease.

Recombinant adenoviral vectors have found broad utility for a variety of gene therapy applications. Their utility for such applications is due largely to the high efficiency of in vivo gene transfer achieved in a variety of organ contexts.

Adenoviral particles may be used to advantage as vehicles for adequate gene delivery. Such virions possess a number of desirable features for such applications, including: structural features related to being a double stranded DNA nonenveloped virus and biological features such as a tropism for the human respiratory system and gastrointestinal tract. Moreover, adenoviruses are known to infect a wide variety of cell types in vivo and in vitro by receptor-mediated endocytosis. Attesting to the overall safety of adenoviral vectors, infection with adenovirus leads to a minimal disease state in humans comprising mild flu-like symptoms.

Due to their large size (~36 kilobases), adenoviral genomes are well suited for use as gene therapy vehicles because they can accommodate the insertion of foreign DNA following the removal of adenoviral genes essential for replication and nonessential regions. Such substitutions render the viral vector impaired with regard to replicative functions and infectivity. Of note, adenoviruses have been used as vectors for gene therapy and for expression of heterologous genes.

It is desirable to introduce a vector that can provide, for example, multiple copies of a desired gene and hence greater amounts of the product of that gene. Improved adenoviral vectors and methods for producing these vectors have been described in detail in a number of references, patents, and patent applications, including: Mitani and Kubo (2002, Curr Gene Ther. 2(2):135-44); Olmsted-Davis et al. (2002, Hum Gene Ther. 13(11):1337-47); Reynolds et al. (2001, Nat Biotechnol. 19(9):838-42); U.S. Pat. No. 5,998,205 (wherein tumor-specific replicating vectors comprising multiple DNA copies are provided); U.S. Pat. No. 6,228,646 (wherein helper-free, totally defective adenovirus vectors are described); U.S. Pat. No. 6,093,699 (wherein vectors and methods for gene therapy are provided); U.S. Pat. No. 6,100,242 (wherein a transgene-inserted replication defective adenovirus vector was used effectively in in vivo gene therapy of peripheral vascular disease and heart disease); and International Patent Application Nos. WO 94/17810 and WO 94/23744.

For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression of the variant or functional fragments thereof. For example, an E1 deleted type 5 adenoviral vector comprising nucleic acid sequences encoding variant under the control of a cytomegalovirus (CMV) promoter may be used to advantage in the methods of the present invention.

Adenoviral vectors for recombinant gene expression have been produced in the human embryonic kidney cell line 293 (Graham et al., 1977, J. Gen. Virol. 36:59-72). This cell line is permissive for growth of adenovirus 2 (Ad2) and adenovirus 5 mutants defective in E1 functions because it comprises the left end of the adenovirus 5 genome and, therefore, expresses E1 proteins. E1 genes integrated into the cellular genome of 293 cells are expressed at levels which facilitate the use of these cells as an expression system in which to amplify viral vectors from which these genes have been deleted. 293 cells have been used extensively for the isolation and propagation of E1 mutants, for helper-independent cloning, and for expression of adenovirus vectors. Expression systems such as the 293 cell line, therefore, provide essential viral functions in trans and thereby enable propagation of viral vectors in which exogenous nucleic acid sequences have been substituted for E1 genes. See Young et al. in The Adenoviruses, Ginsberg, ed., Plenum Press, New York and London (1984), pp. 125-172. Other expression systems well suited to the propagation of adenoviral vectors are known to those of skill in the art (e.g., HeLa cells) and have been reviewed elsewhere.

Also included in the present invention is a method for modulating hemostasis comprising providing cells of an individual with a nucleic acid delivery vehicle encoding a variant polypeptide and allowing the cells to grow under conditions wherein the variant polypeptide is expressed.

From the foregoing discussion, it can be seen that variant polypeptides, and variant polypeptide expressing nucleic acid vectors may be used in the treatment of disorders associated with aberrant blood coagulation.

C. Pharmaceutical Compositions

The expression vectors of the present invention may be incorporated into pharmaceutical compositions that may be delivered to a subject, so as to allow production of a biologically active protein (e.g., a variant polypeptide or functional fragment or derivative thereof). In a particular embodiment of the present invention, pharmaceutical compositions comprising sufficient genetic material to enable a recipient to produce a therapeutically effective amount of a variant polypeptide can influence hemostasis in the subject. Alternatively, as discussed above, an effective amount of the variant polypeptide may be directly infused into a patient in need thereof. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents (e.g., co-factors) which influence hemostasis.

In particular embodiments, the pharmaceutical compositions also contain a pharmaceutically acceptable excipient/carrier. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., 18th Edition, Easton, Pa. [1990]).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, the preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they may be placed in an appropriate container and labeled for treatment. For administration of variant-containing vectors or polypeptides, such labeling would include amount, frequency, and method of administration.

Pharmaceutical compositions suitable for use in the invention include compositions wherein the active ingredients are contained in an effective amount to achieve the intended therapeutic purpose. Determining a therapeutically effective dose is well within the capability of a skilled medical practitioner using the techniques and guidance provided in the present invention. Therapeutic doses will depend on, among other factors, the age and general condition of the subject, the severity of the aberrant blood coagulation phenotype, and the strength of the control sequences regulating the expression levels of the variant polypeptide. Thus, a therapeutically effective amount in humans will fall in a relatively broad range that may be determined by a medical practitioner based on the response of an individual patient to vector-based variant treatment.

D. Administration

Figure 2:
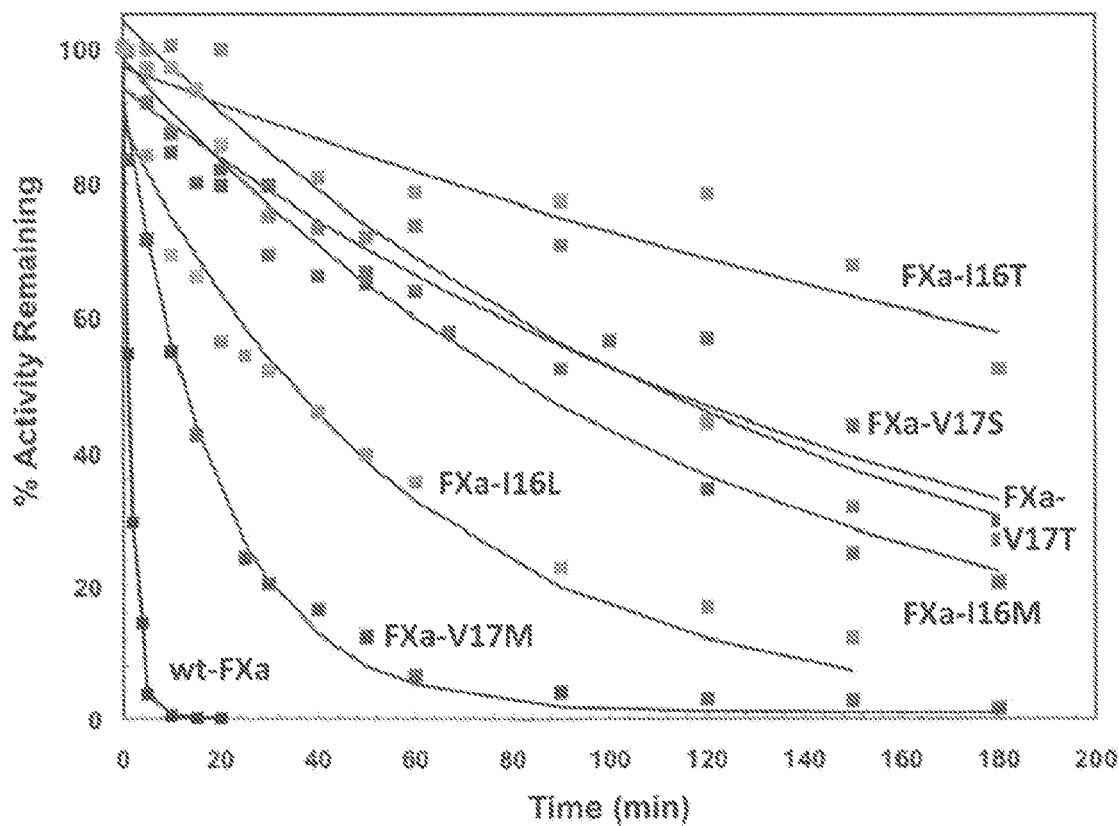
FIG. 2 provides a graph of the activity of wild-type FXa and various FXa variants over time in hemophilia B plasma.

The variant polypeptides, alone or in combination with other agents may be directly infused into a patient in an appropriate biological carrier as described hereinabove. Expression vectors of the present invention comprising nucleic acid sequences encoding variant or functional fragments thereof, may be administered to a patient by a variety of means (see below) to achieve and maintain a prophylactically and/or therapeutically effective level of the variant polypeptide. One of skill in the art could readily determine specific protocols for using the variant encoding expression vectors of the present invention for the therapeutic treatment of a particular patient. Protocols for the generation of adenoviral vectors and administration to patients have been described in U.S. Pat. Nos. 5,998,205; 6,228,646; 6,093,699; 6,100,242; and International Patent Application Nos. WO 94/17810 and WO 94/23744, which are incorporated herein by reference in their entirety.

Variant encoding adenoviral vectors of the present invention may be administered to a patient by any means known. Direct delivery of the pharmaceutical compositions in vivo may generally be accomplished via injection using a conventional syringe, although other delivery methods such as convection-enhanced delivery are envisioned (See e.g., U.S. Pat. No. 5,720,720). In this regard, the compositions may be delivered subcutaneously, epidermally, intradermally, intrathecally, intraorbitally, intramucosally, intraperitoneally, intravenously, intraarterially, orally, intrahepatically or intramuscularly. Other modes of administration include oral and pulmonary administration, suppositories, and transdermal applications. A clinician specializing in the treatment of patients with blood coagulation disorders may determine the optimal route for administration of the adenoviral vectors comprising variant nucleic acid sequences based on a number of criteria, including, but not limited to: the condition of the patient and the purpose of the treatment (e.g., enhanced or reduced blood coagulation).

The present invention also encompasses AAV vectors comprising a nucleic acid sequence encoding a variant polypeptide. Also provided are lentiviruses or pseudo-typed lentivirus vectors comprising a nucleic acid sequence encoding a variant polypeptide. Also encompassed are naked plasmid or expression vectors comprising a nucleic acid sequence encoding a variant polypeptide.

The following example is provided to illustrate various embodiments of the present invention. The example is illustrative and is not intended to limit the invention in any way.

EXAMPLE

The zymogenicity of the FXa variants of the instant invention was determined Specifically, FXa chromogenic substrate activity was measured from initial rates of hydrolysis of Spectrozyme® FXa as previously described (Camire, R. M. (2002) J. Biol. Chem., 277:37863-37870). Briefly, kinetic measurements were performed in 20 mm Hepes, 0.15 m NaCl, 0.1% (w/v) polyethylene glycol 8000, 2 mm $CaCl_2$, pH 7.5 (assay buffer). Wild-type or mutant FXa was incubated with Spectrozyme® FXa. Chromogenic activity was assessed by monitoring the increase in absorbance at 405 nm over time. The kinetics of peptidyl substrate hydrolysis was measured using increasing concentrations of substrate and initiated with FXa. Kinetic parameters were determined by least-squares fitting of the initial rate data to appropriate equations.

As seen in FIG. 1, the FXa variants of the instant invention are less active than wild-type FXa. The relative activity of the FXa variants was determined to be: FXa-V17M>FXa-I16L>FXa-V17T>FXa-I16M>FXa-V17S>FXaI16T.

The half-life of the FXa variants in hemophilia B plasma was then determined. Wild-type FXa and the FXa variants were added to hemophilia B plasma and, at different time points, an aliquot of the mixture was withdrawn and assayed in an aPTT-based assay. The results with hemophilia B plasma (FIG. 2) show that the relative residual activity of wild-type FXa was inhibited very rapidly with a $t_{1/2}$ of 1 minute. In contrast, the activity of the FXa variants persisted for a much longer time. FXa-I16L had a half-life of about 50 minutes. FXa-V17M had a half-life in between wild-type and FXa-I16L ($t_{1/2}$=13 minutes). However, FXa-I16M, FXa-V17T, and FXa-V17S all exhibited longer half-lives of about 100 minutes. Moreover, FXa-I16T exhibited an unexpectedly superior half-life of about 240 minutes. These results indicate that the characteristics of an enzyme may be modulated so that it has a long half-life in plasma and can correct the clotting time of hemophilic plasma.

The inhibition of FXa variants by antithrombin III was also determined Antithrombin III is an important inhibitor of FXa in plasma and in vivo. Table 1 provides the rate constants for inhibition by antithrombin III. These data generally correlate well with the half-life data in FIG. 2 and show that variants with a long half-life (e.g., $FXa^{V17S}$ and $FXa^{I16T}$) are resistant to antithrombin III due to their altered active sites.

TABLE 1

Rate constants for inhibition by antithrombin. FXa and variants were incubated with different amounts of antithrombin III and FXa residual activity was monitored over time. Experiments were performed as detailed in Bunce et al. (2011) Blood 117: 290-298.

|  | $k_2$ (M$^{-1}$ s$^{-1}$) ± SD × 10$^3$ | Fold Difference |
| --- | --- | --- |
| wtFXa | 1.4 ± 0.2 | 1 |
| $FXa^{V17M}$ | 0.1 ± 0.007 | 14 |
| $FXa^{I16M}$ | 0.02 ± 0.001 | 40 |
| $FXa^{V17T}$ | 0.02 ± 0.0008 | 70 |
| $FXa^{V17S}$ | ND | >>100 |
| $FXa^{I16T}$ | ND | >>100 |

ND: not able to determine accurate value.

Figure 3:
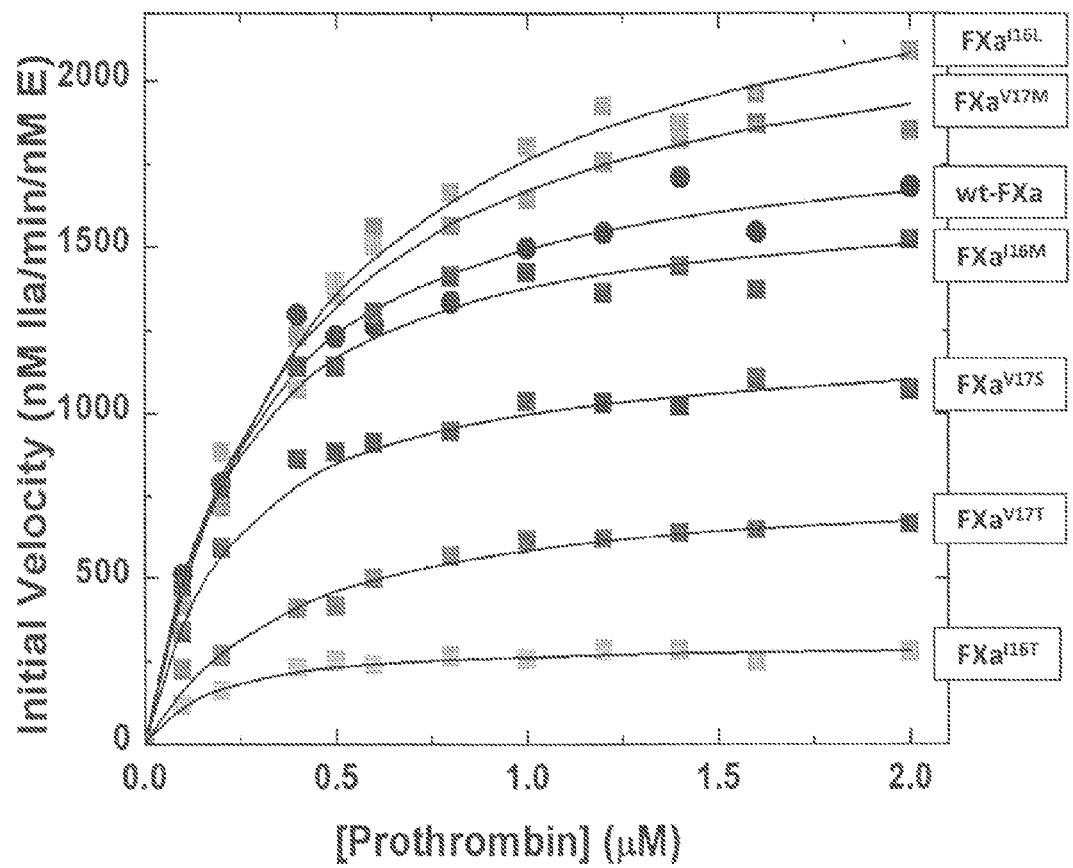
FIG. 3 provides a graph of the kinetics of prothrombin activation with wild-type FXa or the indicated FXa mutants in the presence of FVa and anionic membranes (PCPS).

The kinetics of prothrombin activation by the various mutants was also determined. The results are presented in FIG. 3. Notably, $FXa^{V17M}$ and $FXa^{I16L}$ demonstrated faster than wild-type kinetics, $FXa^{I16M}$ displayed similar to wild-type kinetics, and $FXa^{V17S}$ $FXa^{V17T}$, and $FXa^{I16T}$ were slower than wild-type. These data show that despite altered reactivity with a small substrate (Spec Xa; FIG. 1) and resistance to inhibition by antithrombin III (Table 1), the incorporation of the zymogen-like variants into prothrombinase (e.g., bound to FVa on anionic membranes) largely restored their function with respect to prothrombin activation.

Figure 4A:
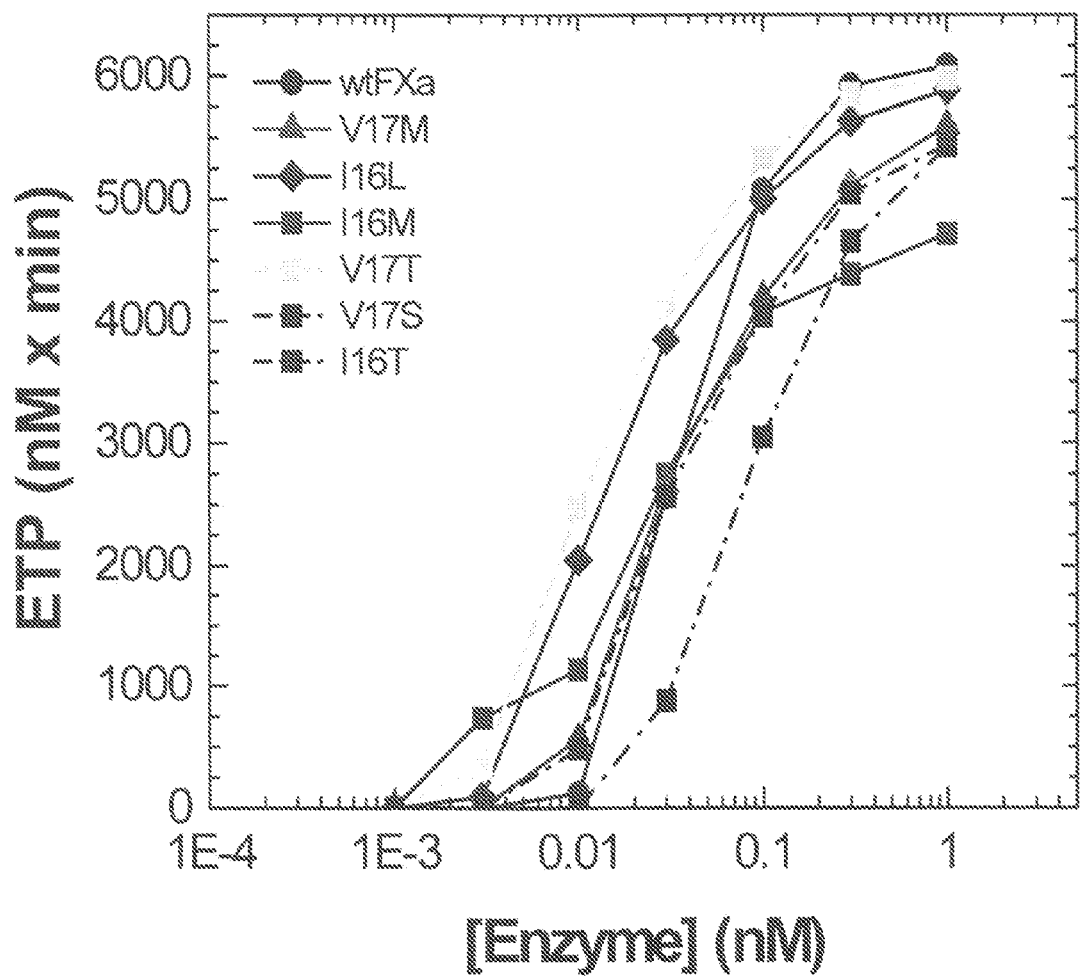
FIG. 4A shows the endogenous thrombin potential (ETP) of wild-type FXa and FXa variants at different concentrations.
Figure 4B:
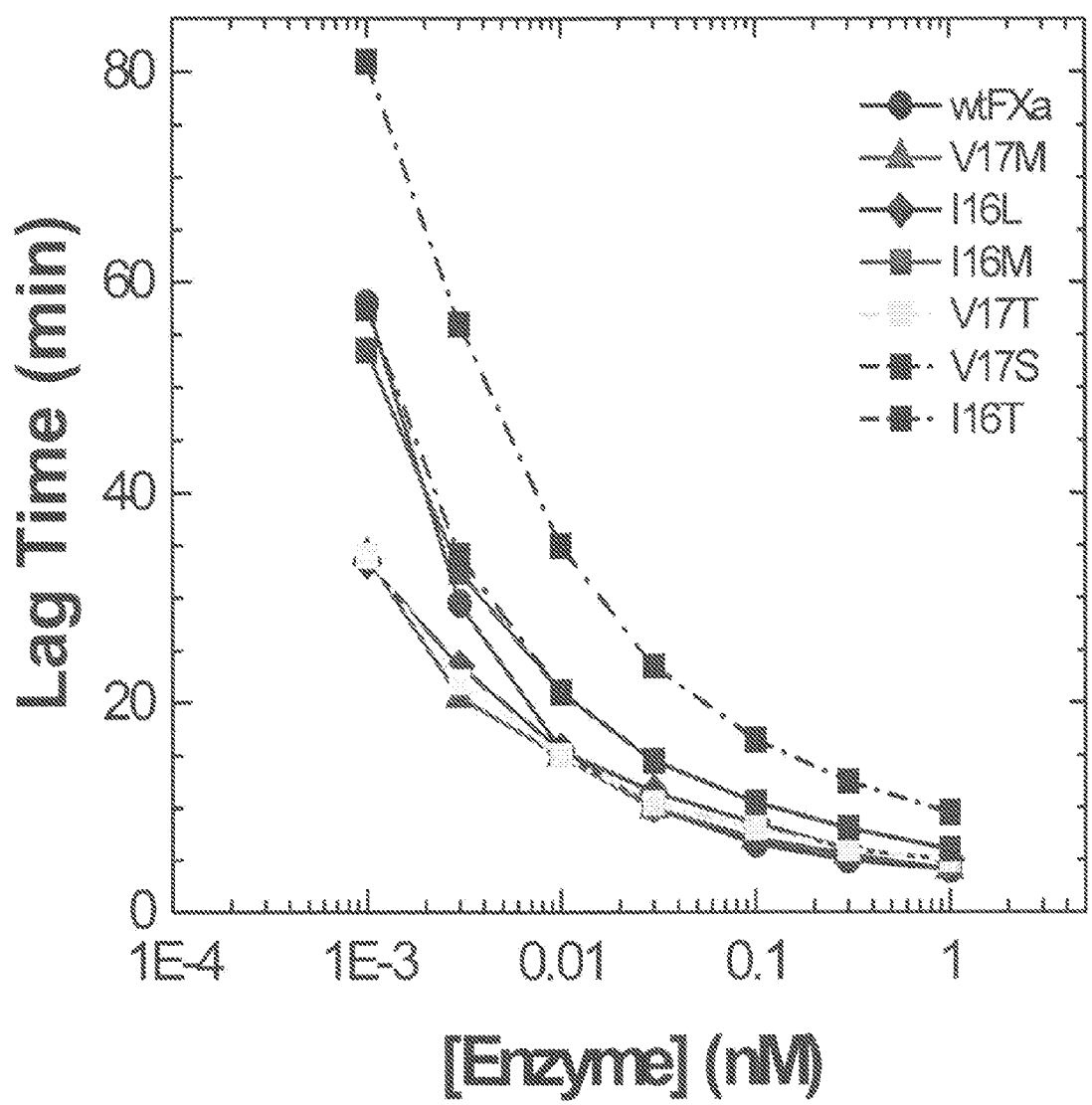
FIG. 4B provides the lag time in thrombin generation of wild-type FXa and FXa variants at different concentrations.

The ability of the FXa variants to restore thrombin generation in hemophilia B plasma was also evaluated. Specifically, a thrombin generation assay (TGA) was performed and the endogenous thrombin potential (ETP) was measured. The TGA assay provides a measure of global coagulability and is a functional assay for quantification of thrombin generation capacity. FIG. 4A shows the endogenous thrombin potential (ETP) of wild-type FXa and FXa variants at different concentrations. FIG. 4B provides the lag time (time to thrombin burst) in thrombin generation of wild-type FXa and FXa variants at different concentrations. The results show that the more zymogen-like the variant, the longer the lag time to the initial burst of thrombin production.

The coagulation parameters of FXa variants in hemophilia B plasma are provided in Table 2. Hemophilic B plasma was spiked with 0.1 nM wild-type FXa to correct the clotting time (activated partial thromboplastin time (aPTT)) of these plasmas. Wild-type FXa gave a clotting time of ~32 seconds. The addition of the same concentration of FXa variants gave clot times which varied from ~41 to 94 seconds. The half-lives of the constructs in hemophilia B plasma (FIG. 2) and the ETP data (FIG. 4) are also provided in Table 2.

TABLE 2

Coagulation parameters of FXa variants in hemophilia B plasma. In all experiments, FXa variants 0.1 nM and FVa 10 nM in human hemophilia B plasma.

| Sample | aPTT (Sec) | aPTT + FVa (sec) | ETP nM min | Time to peak (min) | Peak height (nM) | $t_{1/2}$ (min) |
| --- | --- | --- | --- | --- | --- | --- |
| NHP | 37 ± 0.4 | ND | 5685 | 29 | 367 | ND |
| HB | 110 ± 4 | ND | NA | NA | NA | ND |
| HB + FIX | 40 ± 0.4 | ND | 4773 | 14 | 372 | ND |
| HB + wt-FXa | 32 ± 1 | 25 ± 0.3 | 2727 | 17 | 124 | 1.2 ± 0.1 |
| HB + FXa-V17M | 41 ± 0.4 | 31 ± 1 | 4554 | 14 | 271 | 14 ± 1 |
| HB + FXa-I16L | 54 ± 2 | 33 ± 2 | 3901 | 17 | 203 | 42 ± 4 |
| HB + FXa-I16M | 60 ± 4 | 39 ± 2 | 3336 | 18 | 156 | 84 ± 4 |
| HB + FXa-V17T | 47 ± 2 | 29 ± 1 | 4024 | 15 | 222 | 101 ± 10 |
| HB + FXa-V17S | 76 ± 4 | 45 ± 2 | 3802 | 20 | 173 | 118 ± 9 |
| HB + FXa-I16T | 94 ± 1 | 73 ± 2 | 3375 | 29 | 138.5 | 240 ± 20 |

HB = hemophilia B plasma.
NHP = normal human plasma.

Figure 5:
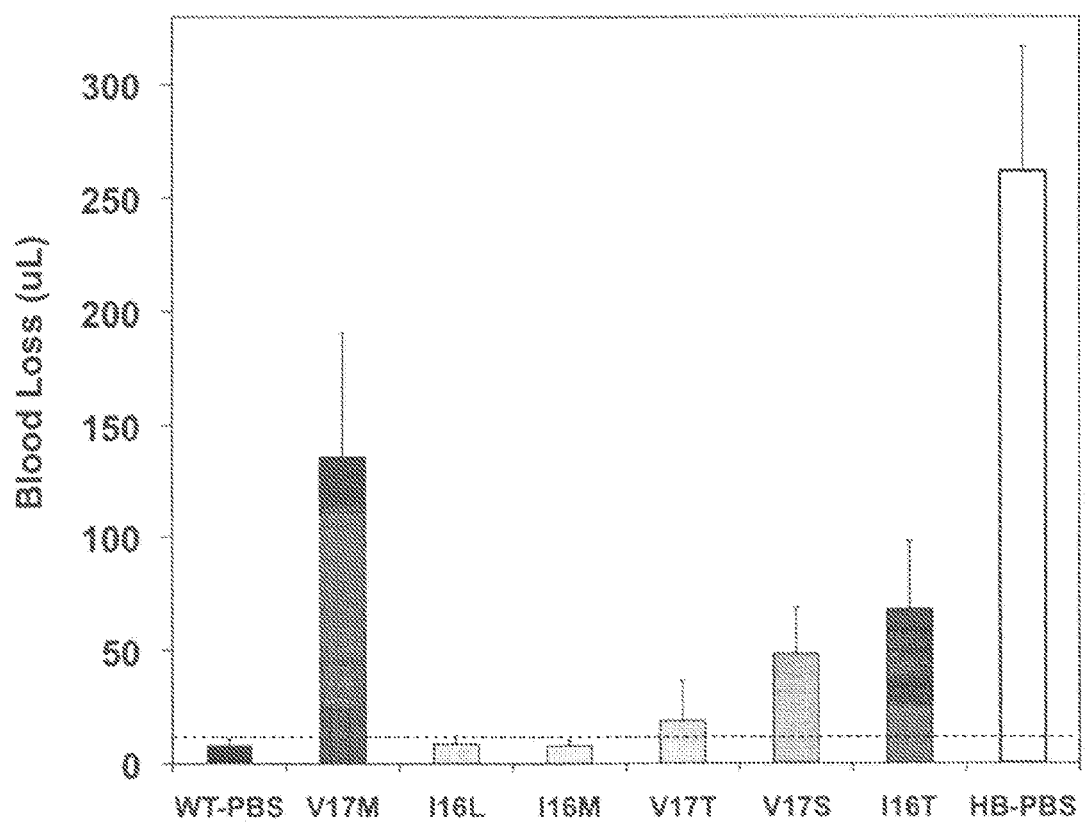
FIG. 5 shows the amount of blood loss in hemophilia B mice in a modified tail clip assay (protein or PBS infusion two minutes post-injury) with administration of the indicated FXa variants or PBS negative control. Dashed line represents amount of blood loss in hemostatically normal mice. Number of mice/group=5-8.

To further test the effectiveness of the FXa variants in vivo, the ability of the FXa variants to reduce blood loss in hemophilia B mice following injury to the tail was determined (Schlachterman et. al. (2005) J. Thromb. Haemost., 3:2730-2737). Blood loss was measured during a 10 minute period after sectioning the distal part of the tail of 6-12 week old mice. In this type of assay, blood loss is minimal in normal wild-type BALB/c mice (PBS injected) and quite substantial in PBS injected hemophilia B mice (BALB/c) following the tail injury (FIG. 5). In contrast, injection of the FXa variants, particularly FXa-I16L, FXa-I16M, FXa-V17T, FXa-V17S, and FXa-I16T, 2 minutes following tail injury significantly reduced the total amount of blood loss following injury (FIG. 5).

Figure 6:
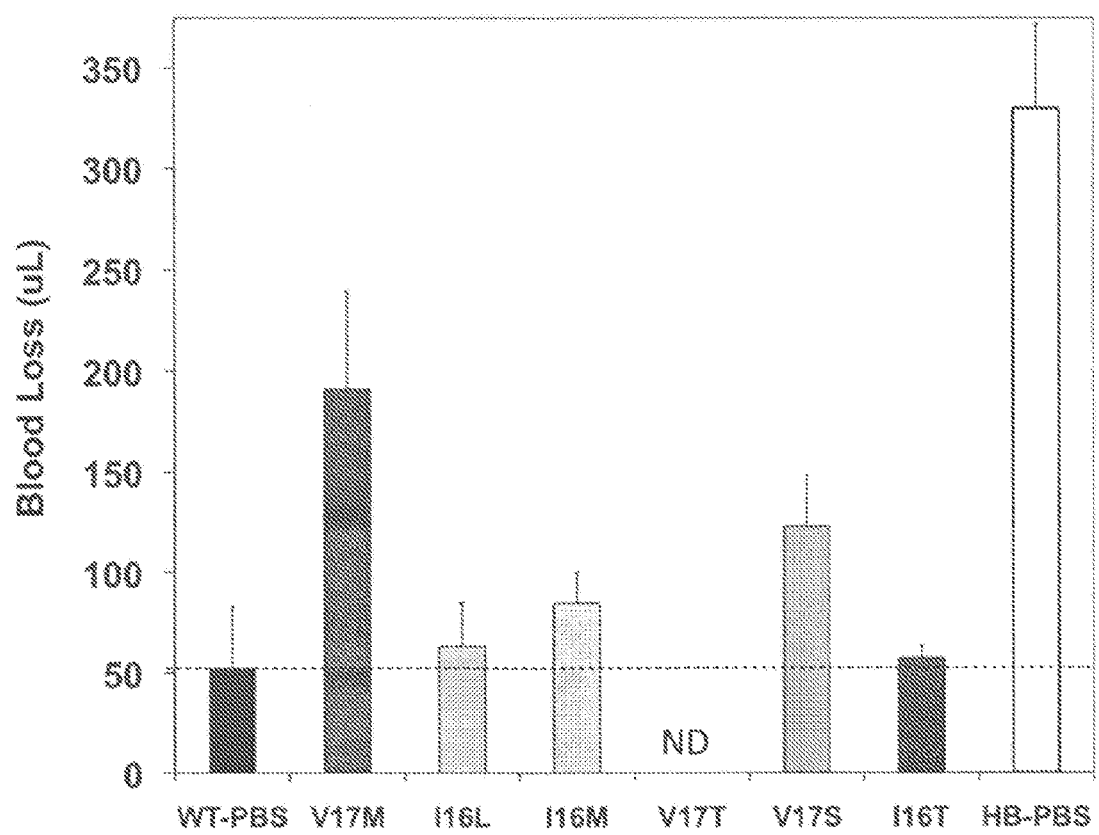
FIG. 6 shows the amount of blood loss in hemophilia B mice in a tail clip assay with a 5 minute pre-infusion of indicated FXa variants or PBS negative control. ND=not determined Dashed line represents amount of blood loss in hemostatically normal mice. Number of mice/group=5-8.
Figure 7:
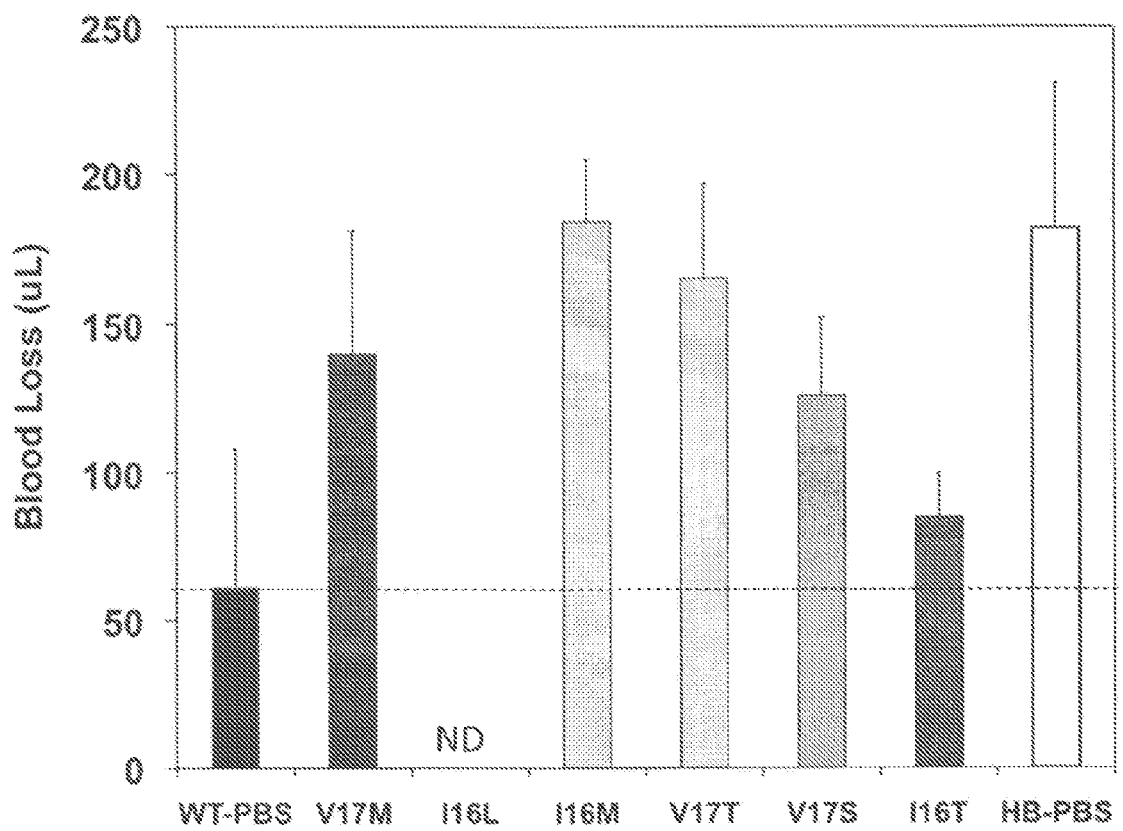
FIG. 7 shows the amount of blood loss in hemophilia B mice in a tail clip assay with a 30 minute pre-infusion of the indicated FXa variants or PBS negative control. ND=not determined Dashed line represents amount of blood loss in hemostatically normal mice. Number of mice/group=5-8.

The ability of the FXa variants to correct the bleeding time of hemophilia B mice following injury to the tail was also assayed when the FXa variant was pre-infused. Specifically, 6-12 week C57BL/6 mice or hemophilia B C57BL/6 mice were injected with PBS or the FXa variant 5 minutes (FIG. 6) or 30 minutes (FIG. 7) prior to tail injury. When the FXa variants were infused 5 minutes prior to injury, the FXa variants, particularly FXa-I16L, FXa-I16M, FXa-V17T, FXa-V17S, and FXa-I16T, significantly reduced the total amount of blood loss following tail injury (FIG. 6). However, when the FXa variants were infused 30 minutes prior to injury, only FXa-I16T significantly reduced the total amount of blood loss following tail injury to near wild-type levels (FIG. 7). This result demonstrates that the increased half-life of FXa-I16T activity observed in hemophilia B plasma is relevant in vivo and allows for proper clotting of wounds long after infusion.

Figure 8:
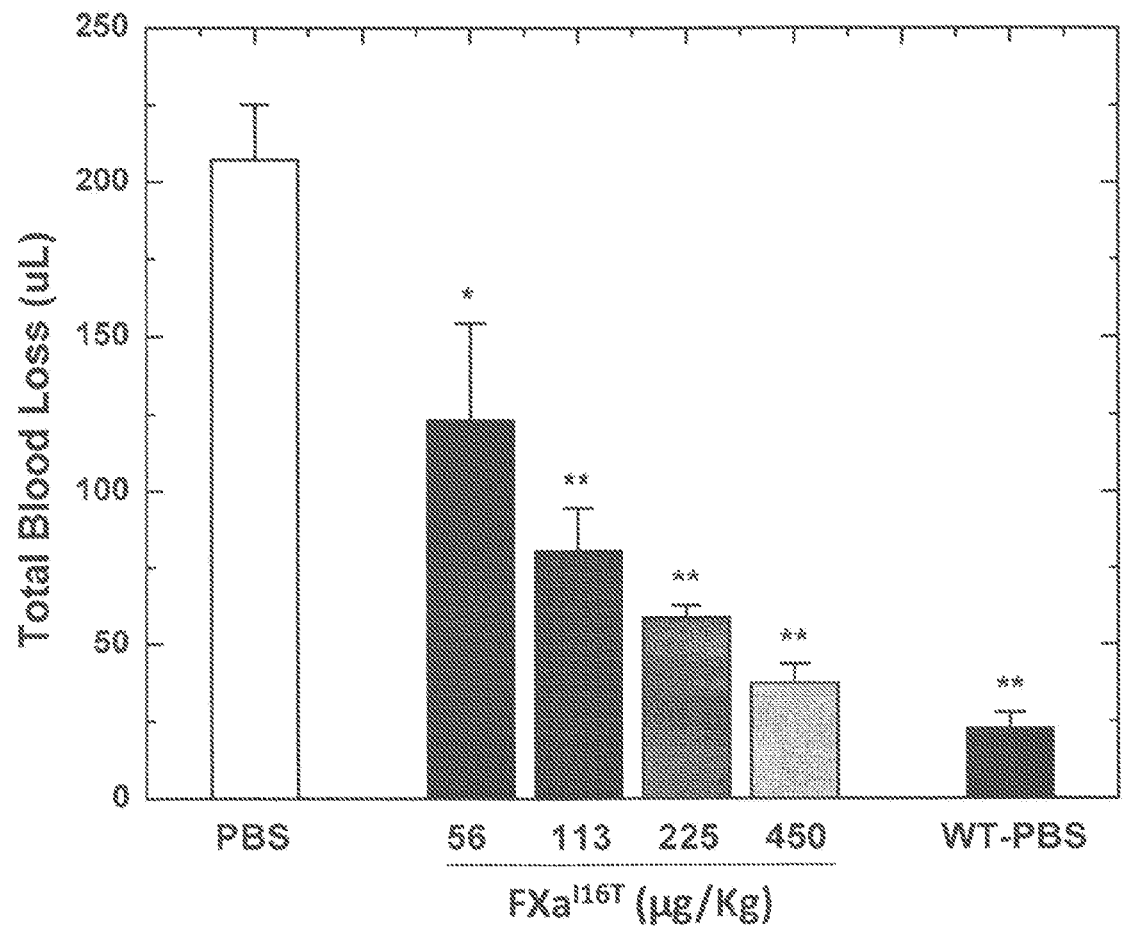
FIG. 8 provides a graph of total blood loss from a tail clip assay of wild-type Balb/c mice or hemophilia B (HB) Balb/c mice infused with PBS or the indicated amounts of $FXa^{I16T}$ five minutes prior to injury. ** p<0.001 vs. HB-PBS. Number of mice/group=5-8.

To further characterize $FXa^{I16T}$, a dose response study in the tail clip assay was performed. $FXa^{I16T}$ at different doses was administered five minutes prior to injury and—as seen in FIG. 8—$FXa^{I16T}$ dose-dependently reduced blood loss in hemophilia B mice following tail injury. At levels of 450 µg/kg, blood loss was reduced to levels seen in wild-type mice.

In a further model, select FXa variants were tested following injury to the carotid artery following application of FeCl$_3$ (7.5%) according to procedures detailed in Ivanciu et al. (2011) Nature Biotechnology 29:1028-1033. In this model, the carotid artery is injured with FeCl$_3$ and blood flow is monitored using a Doppler flow probe and time to vessel occlusion is recorded. Following injury, HB mice do not form a blood clot in the carotid artery while wild-type mice form an occlusion clot at ~15 minutes (Table 3). When the protein was infused 10 minutes after injury, wt-FVa was not effective while FXa-I16M and FXa-I16T yielded occlusive thrombi at ~2-3 minutes. When the protein was infused 15 minutes before the injury, only FXa-I16T was still effective, due to its long half-life.

TABLE 3

Time to carotid artery occlusion following FeCl$_3$-induced injury.

| Geno-type | Sample | Dose μg/kg | Total # of mice | No occlusions (# of mice) | Transient occlusion (# of mice) | Complete occlusion (# of mice) | Time to occlusion (min) |
|---|---|---|---|---|---|---|---|
| Controls | | | | | | | |
| WT | PBS | — | 5 | 0 | 0 | 5 | 15.3 ± 0.8 |
| HB | PBS | — | 5 | 5 | 0 | 0 | — |
| Human proteins - 10 minutes after injury | | | | | | | |
| HB | hwt-FXa | 450 | 5 | 5 | 0 | 0 | — |
| HB | hFXa$^{V17M}$ | 450 | 7 | 0 | 1 | 6 | 3.2 ± 0.3 |
| HB | hFXa$^{I16M}$ | 450 | 7 | 0 | 0 | 7 | 2.0 ± 0.09 |
| HB | hFXa$^{I16T}$ | 450 | 7 | 0 | 0 | 7 | 3.6 ± 0.3 |
| Human proteins - 15 minutes before injury | | | | | | | |
| HB | hFXa$^{V17M}$ | 450 | 7 | 7 | 0 | 0 | — |
| HB | hFXa$^{I16M}$ | 450 | 7 | 6 | 0 | 1 | 7.1 |
| HB | hFXa$^{I16T}$ | 450 | 7 | 1 | 0 | 6 | 9 ± 1.5 |

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A Factor Xa variant which modulates hemostasis wherein
the Ile at position 16 in chymotrypsin numbering system is Thr or Met.
2. The Factor Xa variant of claim 1, wherein the Ile at position 16 is Thr.
3. The Factor Xa variant of claim 1, further comprising a substitution at position 17 in chymotrypsin numbering system.
4. The Factor Xa variant of claim 1, further comprising at least one substitution at position 18, 19, or 194 in chymotrypsin numbering system.
5. The Factor Xa variant of claim 2, wherein all residues other than the Thr at position 16 are wild-type.
6. The Factor Xa variant of claim 1, wherein the Factor Xa variant has a longer plasma half life than wild-type Factor Xa.
7. The Factor Xa variant of claim 1, wherein said Factor Xa comprises a light and heavy chain, wherein the light chain has at least 80% homology with SEQ ID NO: 3, wherein the heavy chain has at least 80% homology with SEQ ID NO: 5 wherein the Ile at position 16 in chymotrypsin numbering system is Thr or Met.
8. The Factor Xa variant of claim 7, wherein the Ile at position 16 is Thr.
9. The Factor Xa variant of claim 7, wherein said light chain is SEQ ID NO: 3 and said heavy chain is SEQ ID NO: 5 wherein the Ile at position 16 in chymotrypsin numbering system is Thr or Met.
10. A composition comprising at least one Factor Xa variant of claim 1 and at least one pharmaceutically acceptable carrier.
11. A method for treatment of a hemostasis related disorder in a patient in need thereof comprising administration of a therapeutically effective amount of the Factor Xa variant of claim 1 in a pharmaceutically acceptable carrier.
12. The method of claim 11, wherein said hemostasis related disorder is selected from the group consisting of hemophilia A, hemphilia B, hemophilia A and B associated with inhibitory antibodies, coagulation factor deficiency, vitamin K epoxide reductase C1 deficiency, gamma-carboxylase deficiency, bleeding associated with trauma, injury, thrombosis, thrombocytopenia, stroke, coagulopathy, disseminated intravascular coagulation (DIC); over-anticoagulation treatment disorders, Bernard Soulier syndrome, Glanzman thromblastemia, and storage pool deficiency.
13. The method of claim 12, wherein said coagulation factor deficiency is a deficiency of a coagulation factor selected from the group consisting of at least one of factor VII, factor IX, factor X, factor XI, factor V, factor XII, factor II, and von Willebrand factor.
14. The method of claim 12, wherein said over-anticoagulation treatment disorder results from administration of heparin, low molecular weight heparin, pentasaccharide, warfarin, small molecule antithrombotics and FXa inhibitors.
15. An isolated nucleic acid encoding the Factor Xa variant of claim 1.
16. An isolated nucleic acid molecule encoding a human Factor X variant, wherein said Factor X variant comprises at least one substitution selected from the group consisting of:
a) the Ile at position 16 in chymotrypsin numbering system is Thr or Met, and
b) the Val at position 17 in chymotrypsin numbering system is Thr or Ser.
17. The nucleic acid molecule of claim 16, wherein the Ile at position 16 is Thr.
18. The nucleic acid molecule of claim 16, wherein the Val at position 17 is Thr.
19. The nucleic acid molecule of claim 16, wherein the Val at position 17 is Ser.
20. The nucleic acid molecule of claim 16, wherein said nucleic acid molecule encodes an intracellular cleavage site, wherein said intracellular cleavage site is between positions 15 and 16 in chymotrypsin numbering system or replaces the activation peptide.
21. The nucleic acid molecule of claim 20, wherein said intracellular protease cleavage site is a PACE/furin cleavage site.
22. The nucleic acid molecule of claim 16, wherein said Factor X variant comprises a propeptide sequence and/or signal peptide.
23. The nucleic acid molecule of claim 16, wherein said FX polypeptide further comprises (i) a propeptide sequence derived from prothrombin, (ii) an intracellular protease cleavage site comprising amino acids RKR replacing the Activation Peptide sequence, and (iii) substitution of the amino acid corresponding to Ile 16 by Thr.
24. An expression vector comprising the nucleic acid of claim 16 operably linked to a regulatory sequence.
25. The vector of claim 24, selected from the group consisting of an adenoviral vector, an adenovirus-associated vector, a retroviral vector, a plasmid, and a lentiviral vector.
26. A host cell comprising the vector of claim 24.
27. The host cell of claim 26, wherein said host cells are CHO cells.
28. A method of producing activated Factor X (FXa) comprising incubating the host cell of claim 27 and purifying the FXa produced thereby.
29. A Factor Xa variant which modulates hemostasis wherein the Val at position 17 in chymotrypsin numbering system is Thr or Ser.
30. The Factor Xa variant of claim 29, wherein the Val at position 17 is Thr.
31. The Factor Xa variant of claim 29, wherein the Val at position 17 is Ser.
32. The Factor Xa variant of claim 29, further comprising a substitution at position 16 in chymotrypsin numbering system.
33. The Factor Xa variant of claim 29, further comprising at least one substitution at position 18, 19, or 194 in chymotrypsin numbering system.
34. The Factor Xa variant of claim 29, wherein the Factor Xa variant has a longer plasma half life than wild-type Factor Xa.
35. The Factor Xa variant of claim 29, wherein said Factor Xa comprises a light and heavy chain, wherein the light chain has at least 80% homology with SEQ ID NO: 3, wherein the heavy chain has at least 80% homology with SEQ ID NO: 5 wherein the Val at position 17 in chymotrypsin numbering system is Thr or Ser.
36. The Factor Xa variant of claim 35, wherein said light chain is SEQ ID NO: 3 and said heavy chain is SEQ ID NO: 5 wherein the Val at position 17 in chymotrypsin numbering system is Thr or Ser.
37. A composition comprising at least one Factor Xa variant of claim 29 and at least one pharmaceutically acceptable carrier.
38. A method for treatment of a hemostasis related disorder in a patient in need thereof comprising administration of a therapeutically effective amount of the Factor Xa variant of claim 31 in a pharmaceutically acceptable carrier.
39. The method of claim 38, wherein said hemostasis related disorder is selected from the group consisting of hemophilia A, hemphilia B, hemophilia A and B associated with inhibitory antibodies, coagulation factor deficiency, vitamin K epoxide reductase C1 deficiency, gamma-carboxylase deficiency, bleeding associated with trauma, injury, thrombosis, thrombocytopenia, stroke, coagulopathy, disseminated intravascular coagulation (DIC); over-anticoagulation treatment disorders, Bernard Soulier syndrome, Glanzman thromblastemia, and storage pool deficiency.

40. The method of claim 39, wherein said coagulation factor deficiency is a deficiency of a coagulation factor selected from the group consisting of at least one of factor VII, factor IX, factor X, factor XI, factor V, factor XII, factor II, and von Willebrand factor.

41. The method of claim 39, wherein said over-anticoagulation treatment disorder results from administration of heparin, low molecular weight heparin, pentasaccharide, warfarin, small molecule antithrombotics and FXa inhibitors.

* * * * *